United States Patent
Loerner

(10) Patent No.: US 11,615,526 B2
(45) Date of Patent: Mar. 28, 2023

(54) SYSTEM AND METHOD OF UTILIZING ONE OR MORE IMAGES OF AN EYE IN MEDICAL PROCEDURES

(71) Applicant: Alcon Inc., Fribourg (CH)

(72) Inventor: Johannes Loerner, Roßtal (DE)

(73) Assignee: Alcon Inc., Fribourg (CH)

( * ) Notice: Subject to any disclaimer, the term of this patent is extended or adjusted under 35 U.S.C. 154(b) by 204 days.

(21) Appl. No.: 16/814,511

(22) Filed: Mar. 10, 2020

(65) Prior Publication Data

US 2020/0311918 A1  Oct. 1, 2020

Related U.S. Application Data

(60) Provisional application No. 62/824,603, filed on Mar. 27, 2019.

(51) Int. Cl.
*G06T 7/00* (2017.01)
*A61B 34/10* (2016.01)
*A61B 3/00* (2006.01)
*A61B 3/12* (2006.01)

(52) U.S. Cl.
CPC .......... *G06T 7/0012* (2013.01); *A61B 3/0058* (2013.01); *A61B 3/1216* (2013.01); *A61B 34/10* (2016.02); *A61B 2034/107* (2016.02); *G06T 2207/30041* (2013.01)

(58) Field of Classification Search
None
See application file for complete search history.

(56) References Cited

U.S. PATENT DOCUMENTS

| | | | |
|---|---|---|---|
| 8,398,236 B2 | 3/2013 | Juhasz | |
| 8,459,794 B2 | 6/2013 | Juhasz | |
| 8,753,321 B2 * | 6/2014 | Mrochen | A61F 9/009 606/5 |
| 9,532,708 B2 | 1/2017 | Juhasz | |
| 2006/0192921 A1 | 8/2006 | Loesel | |

(Continued)

FOREIGN PATENT DOCUMENTS

| | | | |
|---|---|---|---|
| CA | 2909717 A1 | 10/2014 | |
| CN | 103930016 B * | 11/2016 | A61B 3/10 |

(Continued)

OTHER PUBLICATIONS

Machine translation of CN-103930016-B (Year: 2016).*

(Continued)

*Primary Examiner* — Vu Le
*Assistant Examiner* — Courtney Joan Nelson

(57) ABSTRACT

The disclosure provides a system that may acquire, via an image sensor, an image of an eye of a person; may determine a location of an iris of the eye from the image; may determine a position of a suction ring from the image; may display, via a display, the image; may display, via the display, a first graphic overlay on the image that indicates the location of the iris of the eye; may display, via the display, a second graphic overlay on the image that indicates the position of the suction ring; may determine multiple iris structures from the image; may determine an orientation of the eye based at least on the multiple iris structures from the image; and may display, via the display, information that indicates the orientation of the eye.

16 Claims, 24 Drawing Sheets

(56) References Cited

U.S. PATENT DOCUMENTS

| | | | |
|---|---|---|---|
| 2013/0338649 A1 | 12/2013 | Hanebuchi | |
| 2014/0114297 A1* | 4/2014 | Woodley | A61B 34/25 |
| | | | 606/4 |
| 2014/0128731 A1* | 5/2014 | Gonzalez | A61F 9/008 |
| | | | 600/427 |
| 2014/0276677 A1 | 9/2014 | Brownell | |
| 2017/0189233 A1* | 7/2017 | Dewey | A61F 9/00827 |

FOREIGN PATENT DOCUMENTS

| | | | |
|---|---|---|---|
| EP | 2322083 A1 | 5/2011 | |
| JP | 2015163092 A * | 9/2015 | A61F 9/00825 |
| WO | WO-2014172545 A1 * | 10/2014 | A61B 3/107 |
| WO | WO-2014172621 A2 * | 10/2014 | A61B 3/10 |

OTHER PUBLICATIONS

Jonathan H. Talamo, Philip Gooding, David Angeley, William W. Culbertson, Georg Schuele, Daniel Andersen, George Marcellino, Emma Essock-Burns, Juan Batlle, Rafael Feliz, Neil J. Friedman, Daniel Palanker, Optical patient interface in femtosecond laser-assisted cataract surgery: (Year: 2013).*

[Continued reference V]: Contact corneal applanation versus liquid immersion, Journal of Cataract & Refractive Surgery, vol. 39, Issue 4, 2013, pp. 501-510, ISSN 0886-3350, https://doi.org/10.1016/j.jcrs.2013.01.021. (Year: 2013).*

Machine translation of JP-2015163092-A (Year: 2015).*

Qian Liu, et al; "Comparison of corneal flaps created by WavelightFS200 and Intralase FS60 femtosecond lasers"; Clinical Research; Int J Ophthalmol; Jul. 18, 2016; pp. 1006-1010; vol. 9; No. 7.

* cited by examiner

SYSTEM AND METHOD OF UTILIZING ONE OR MORE IMAGES OF AN EYE IN MEDICAL PROCEDURES

BACKGROUND

Field of the Disclosure

The present disclosure relates to ophthalmic surgery and surgical equipment, and more specifically, to systems and methods associated with utilizing one or images of an eye in medical procedures.

Description of the Related Art

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Refractive eye surgery, for example, is a type of ophthalmic surgery used to improve the refractive state of the eye for the purpose of decreasing or eliminating dependency on glasses or contact lenses. Refractive surgery procedures may include surgically remodeling the cornea and/or cataract surgery, either of which may be performed by one or more lasers.

In various ophthalmic surgical procedures, a laser can use photodisruption to create incisions. When performing ophthalmic surgery with a laser, a surgical procedure typically includes docking, imaging, analysis, and laser treatment. During docking, a patient's eye is docked to a suction cone in order to provide pressure to flatten the patient's cornea (known as applanation) and hold it in position for the laser treatment. Docking is a sensitive process, and proper placement of the suction ring in the Z-direction, and in the X and Y-directions, is important for successful ophthalmic surgery.

SUMMARY

The present disclosure provides a system able to acquire, via at least one image sensor, at least an image of an eye of a person. In one example, the at least one image sensor may include at least one camera. In a second example, the at least one image sensor may include multiple image sensors. In another example, the at least one image of the eye may include multiple images of the eye. The system may further determine a location of an iris of the eye from the at least the image of the eye and may further determine a position of a suction ring from the at least the image of the eye. For example, the system may determine the position of the suction ring from the at least the image of the eye before the suction ring is docked with the eye. The suction ring may be docked with the eye for a medical procedure. The system may further display, via a display, the at least the image of the eye. For example, a microscope integrated display may include the display. The system may include the microscope integrated display. The system may further may further display, via the display, a first graphic overlay on the at least the image of the eye that indicates the location of the iris of the eye and may further display, via the display, a second graphic overlay on the at least the image of the eye that indicates the position of the suction ring. For example, the second graphic overlay may provide guidance to a physician or a surgeon in docking the suction ring with the eye. The system may further determine multiple iris structures from the at least the image of the eye. In one example, the multiple iris structures may provide one or more bases for one or more orientations associated with the eye. In another example, the multiple iris structures may provide one or more bases for one or more measurements associated with the eye. The system may further determine an orientation of the eye based at least on the multiple iris structures from the at least the image of the eye and may further display, via the display, information that indicates the orientation of the eye. For example, the information that indicates the orientation of the eye may include a graphic overlay that represents a reticle associated with the orientation of the eye.

The system may further display, via the display, a graphic overlay that represents a reticle associated with an orientation of the suction ring. For example, the reticle associated with the orientation of the suction ring may provide guidance to a physician or a surgeon in docking the suction ring with the eye. The system may further determine at least one incision site based at least on the multiple iris structures from the at least the image of the eye and may further display, via the display, a graphic overlay that indicates the at least one incision site. Determining the at least one incision site may include determining multiple incision sites. The system may further display, via the display, multiple graphic overlays that indicate respective multiple incision sites. For example, the system may concurrently display, via the display, the multiple graphic overlays that indicate the respective multiple incision sites. The system may further determine an angular measurement from an iris structure of the multiple iris structures with respect to a center of a pupil of the eye. For example, the system may display, via the display, the graphic overlay that indicates the at least one incision site based at least on the angular measurement.

The present disclosure further includes a non-transient computer-readable memory device with instructions that, when executed by a processor of a system, cause the system to perform the above steps. The present disclosure further includes a system or a non-transient computer-readable memory device as described above with one or more of the following features, which may be used in combination with one another unless clearly mutually exclusive: i) acquire, via at least one image sensor, at least an image of an eye of a person; ii) determine a location of an iris of the eye from the at least the image of the eye; iii) determine a position of a suction ring from the at least the image of the eye; iv) display, via a display, the at least the image of the eye; vi) display, via the display, a first graphic overlay on the at least the image of the eye that indicates the location of the iris of the eye; vii) display, via the display, a second graphic overlay on the at least the image of the eye that indicates the position of the suction ring; viii) determine multiple iris structures from the at least the image of the eye; ix) determine an orientation of the eye based at least on the multiple iris structures from the at least the image of the eye; x) display, via the display, information that indicates the orientation of the eye; xi) display, via the display, a graphic overlay that represents a reticle associated with the orientation of the eye; xii) display, via the display, a graphic overlay that represents a reticle associated with an orientation of the suction ring; xiii) determine a location of a pupil of the eye from the at least the image of the eye; xiv) display, via the display, a graphic overlay on the at least the image of the eye that indicates the position of the location of the pupil of the eye; xv) determine at least one incision site based at least on the multiple iris structures from the at least the image of the eye; xvi) display, via the display, a graphic overlay that indicates the at least one incision site; and xvii) determine an angular measurement from an iris structure of the multiple iris structures with respect to a center of a pupil of the eye.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
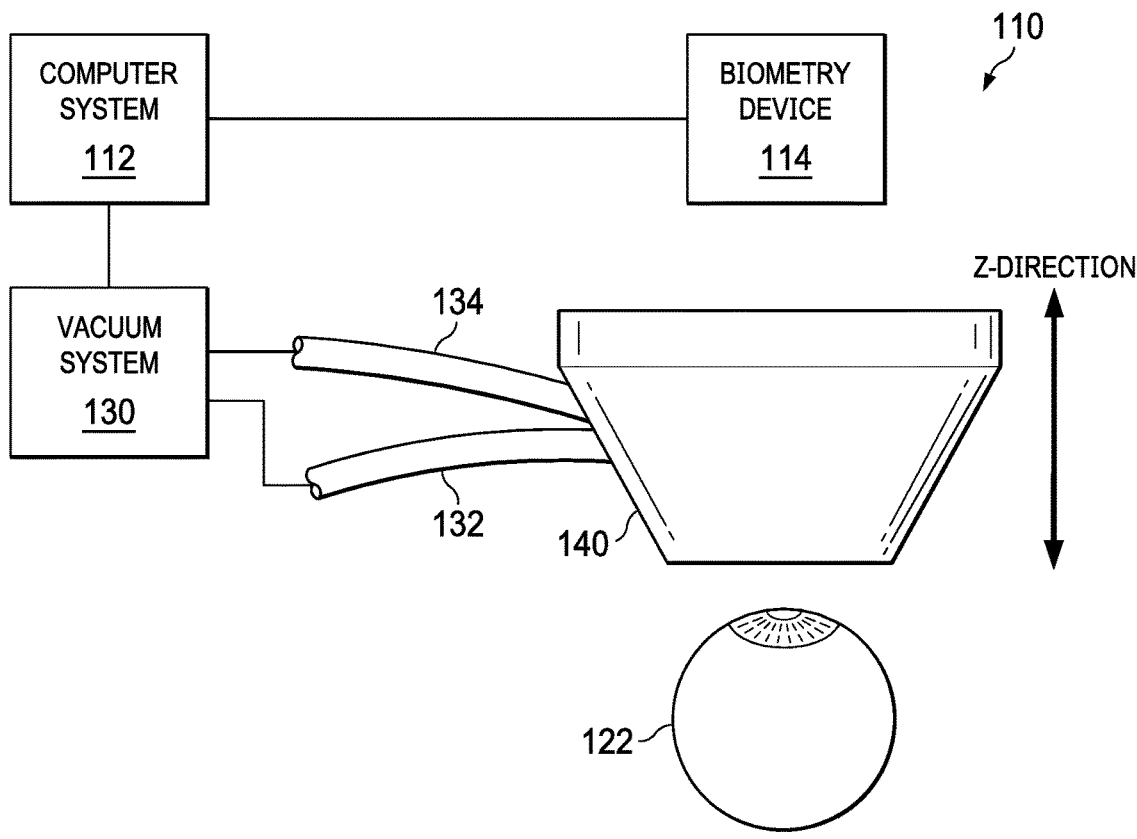
FIG. 1A illustrates an example of a medical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

At a beginning of a medical procedure (e.g., an ophthalmic surgical procedure), a patient may be placed on a support facing upward. For example, the support may be or include a couch, table, or a bed, among others. Prior to the medical procedure, one or more components of a docking apparatus may be docked to an eye of the patient. For example, the one or more components of the docking apparatus may include one or more of a suction ring, a suction cone, and a lens, among others. A laser eye surgery system may include the suction cone and the lens, among others. For example, the laser eye surgery system may include a femtosecond laser, which may include the suction cone and the lens, among others.

A surgeon may manually position the suction ring on the eye. For example, the surgeon may place the suction ring on the eye with no aid from a guidance system. An incorrectly placed suction ring may lead to the eye being tilted. For example, if the eye is tilted, a medical procedure (e.g., a surgical procedure) may not be fully effective, as the suction ring was not centered on an optical axis of the eye. When the medical procedure includes one or more refractive incisions, the medical procedure may not be fully effective if the eye is tilted.

The physician may utilize a guidance system to place a suction ring on an eye. For example, the guidance system may aid the physician in placing the suction ring on the eye such that the suction ring is aligned or closely aligned with an optical axis of the eye. The optical axis of the eye may be associated with a center of a pupil of the eye. For example, utilizing a guidance system to place a suction ring on an eye may provide one or more advantages, which may include guiding a physician in placing a suction ring that is aligned or closely aligned with an optical axis of an eye and in placing a suction ring that is rotationally aligned or closely rotationally aligned with an eye, among others.

An eye of a patient may not be motionless. For example, the eye of the patient may move during a docking process. The eye of the patient may move left and/or right during the docking process, may move up and/or down during the docking process, and/or may rotate clockwise and/or counterclockwise during the docking process. A guidance system may determine one or more movements of the eye of the patient during the docking process. For example, the guidance system may track the eye of the patient. Tracking the eye of the patient may include determining one or more positions of the eye of the patient during and/or after one or more movements of the eye of the patient. For example, the guidance system may display information that indicates the one or more positions of the eye of the patient during and/or after one or more movements of the eye of the patient. The information that indicates the one or more positions of the eye of the patient during and/or after one or more movements of the eye of the patient may aid and/or guide a physician in docking a suction ring to the eye of the patient. For example, the information that indicates the one or more positions of the eye of the patient during and/or after one or more movements of the eye of the patient may be displayed over one or more images of the eye of the patient. The guidance system may augment the one or more images of the eye of the patient with the information that indicates the one or more positions of the eye of the patient during and/or after one or more movements of the eye of the patient. For example, the guidance system may include one or more structures and/or one or more functionalities of an augmented reality (AR) system, an AR method, and/or an AR process. As described further below, a medical system may include one or more structures and/or functionalities of the guidance system. For example, the medical system may aid and/or guide a physician in docking a suction ring to the eye of the patient.

Turning now to FIG. 1A, a first example of a medical system is illustrated. As shown, a medical system 110 may include a computer system 112. As illustrated, medical system 110 may include a biometry device 114. As shown, biometry device 114 may be communicatively coupled to computer system 112. As illustrated, medical system 110 may include a vacuum system 130. As shown, vacuum system 130 may be communicatively coupled to computer system 112. For example, computer system may control vacuum system 130. Vacuum system 130 may create one or more low pressures via one or more of lines 132 and 134. For example, vacuum system 130 may create one or more low pressures via line 134 to adhere and/or seal a suction ring 140 to an eye 122 of a patient. As shown, medical system 110 may include lines 132 and 134 and suction ring 140.

Figure 1B:
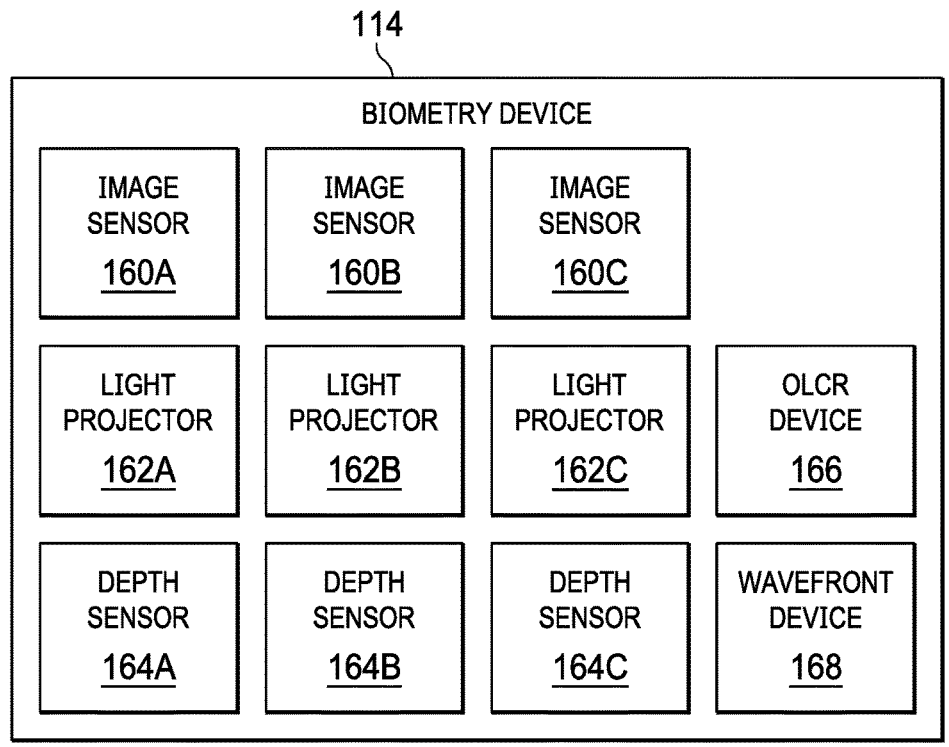
FIG. 1B illustrates an example of a biometry device.

Turning now to FIG. 1B, an example of a biometry device is illustrated. As shown, biometry device 114 may include image sensors 160A-160C. For example, an image sensor 160 may include a camera. As illustrated, biometry device 114 may include light projectors 162A-162C. In one example, a light projector 162 may project visible light. In another example, a light projector 162 may project infrared light. A light projector 162 may project circles and/or dots onto an eye of a patient. An image sensor 160 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 114 may include depth sensors 164A-164C. A depth sensor 164 may include a light projector 162. A depth sensor 164 may include an optical sensor. As illustrated, biometry device 114 may include an optical low coherence reflectometer (OLCR) device 166. As shown, biometry device 114 may include a wavefront device 168.

Wavefront device 168 may include one or more of a light source and a wavefront sensor, among others. A light source may provide a first light wave to eye 122. A wavefront sensor may receive a first perturbed light wave, based at least on the first light wave, from eye 122. In one example, wavefront device 168 may determine first optical corrections based at least on the first perturbed light. In another example, a computer system may determine first optical corrections based at least on the first perturbed light. Wavefront device 168 may provide data, based at least on the first perturbed light wave, to a computer system. For example, the computer system may determine first optical corrections based at least on the data from wavefront device 168.

Any two or more of an image sensor 160, a light projector 162, a depth sensor 164, an OLCR device 166, and a wavefront device 168 may be combined. One or more of image sensors 160A-160C, one or more of light projectors 162A-162C, one or more of depth sensors 164A-164C, OLCR device 166, and/or wavefront device 168, among others, may produce data that may be utilized by a computer system.

Figure 1C:
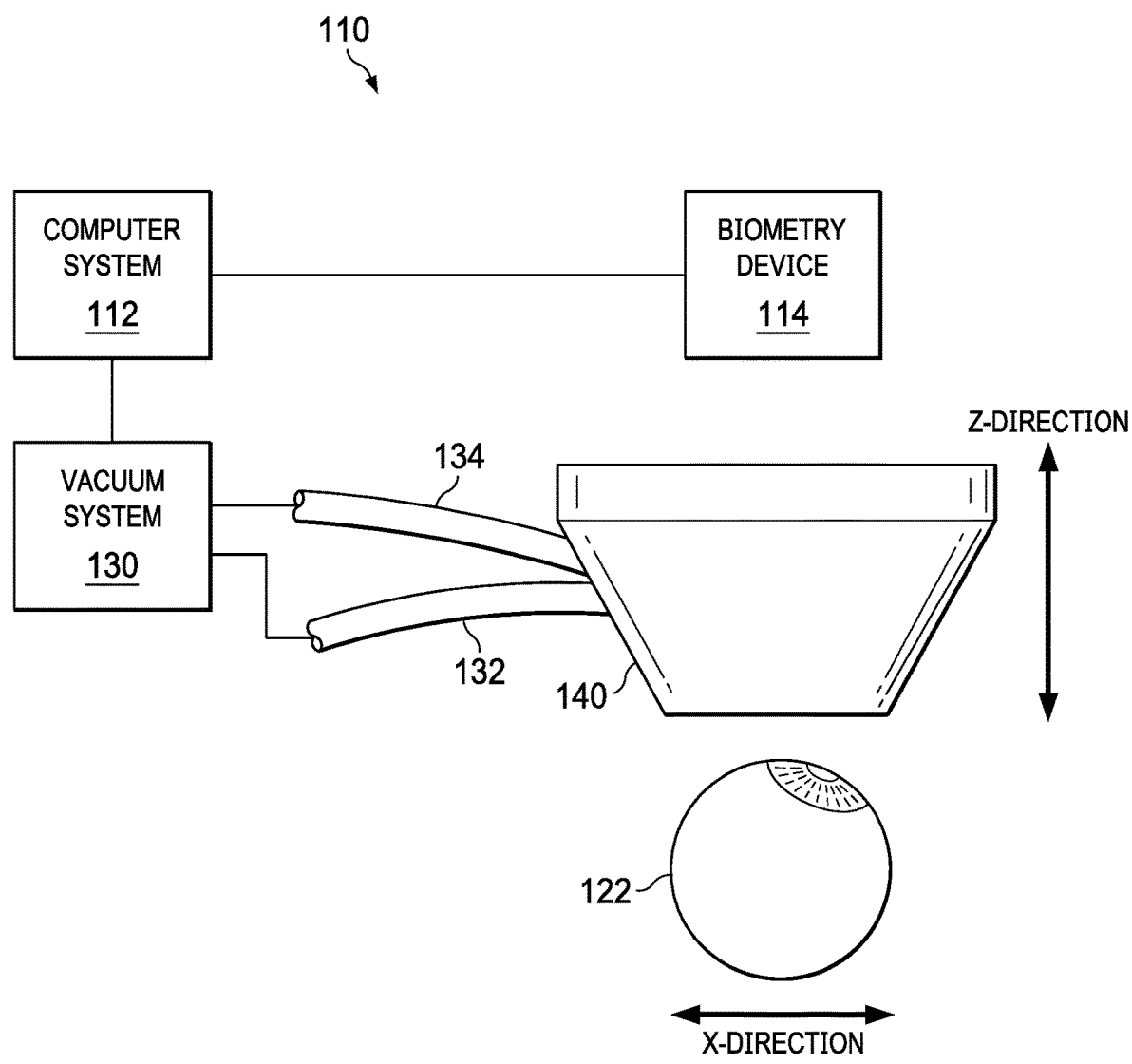
FIG. 1C illustrates an example of an eye tilted in an x-direction.

Turning now to FIG. 1C, an example of an eye tilted in an x-direction is illustrated. As shown, eye 122 may be tilted with respect to an x-direction. For example, suction ring 140 may not be properly placed on eye 122 if suction ring 140 is directly lowered in a z-direction.

Figure 1D:
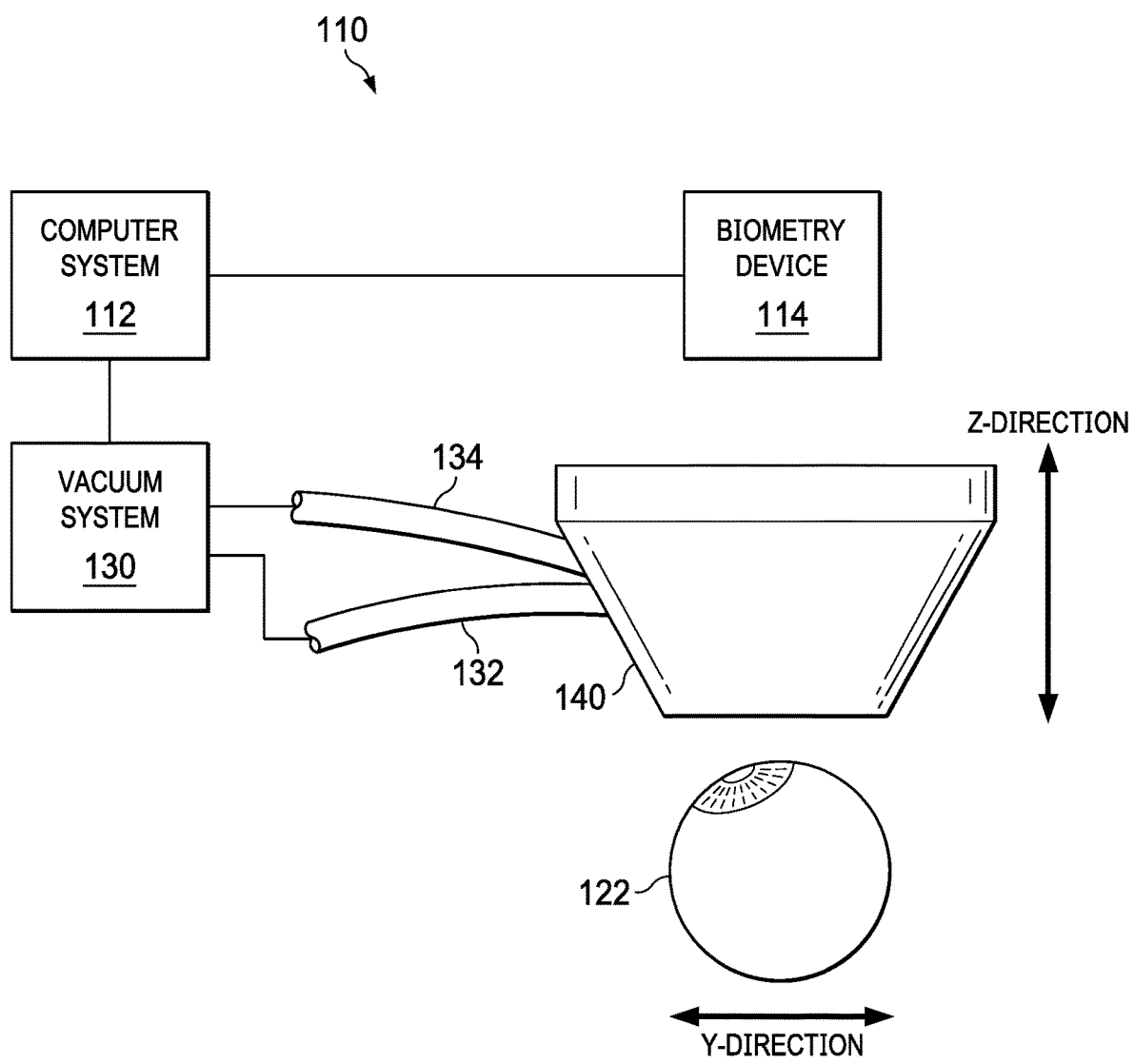
FIG. 1D illustrates an example of an eye tilted in a y-direction.

Turning now to FIG. 1D, an example of an eye tilted in a y-direction is illustrated. As shown, eye 122 may be tilted with respect to a y-direction. For example, suction ring 140 may not be properly placed on eye 122 if suction ring 140 is directly lowered in the z-direction.

Figure 1E:
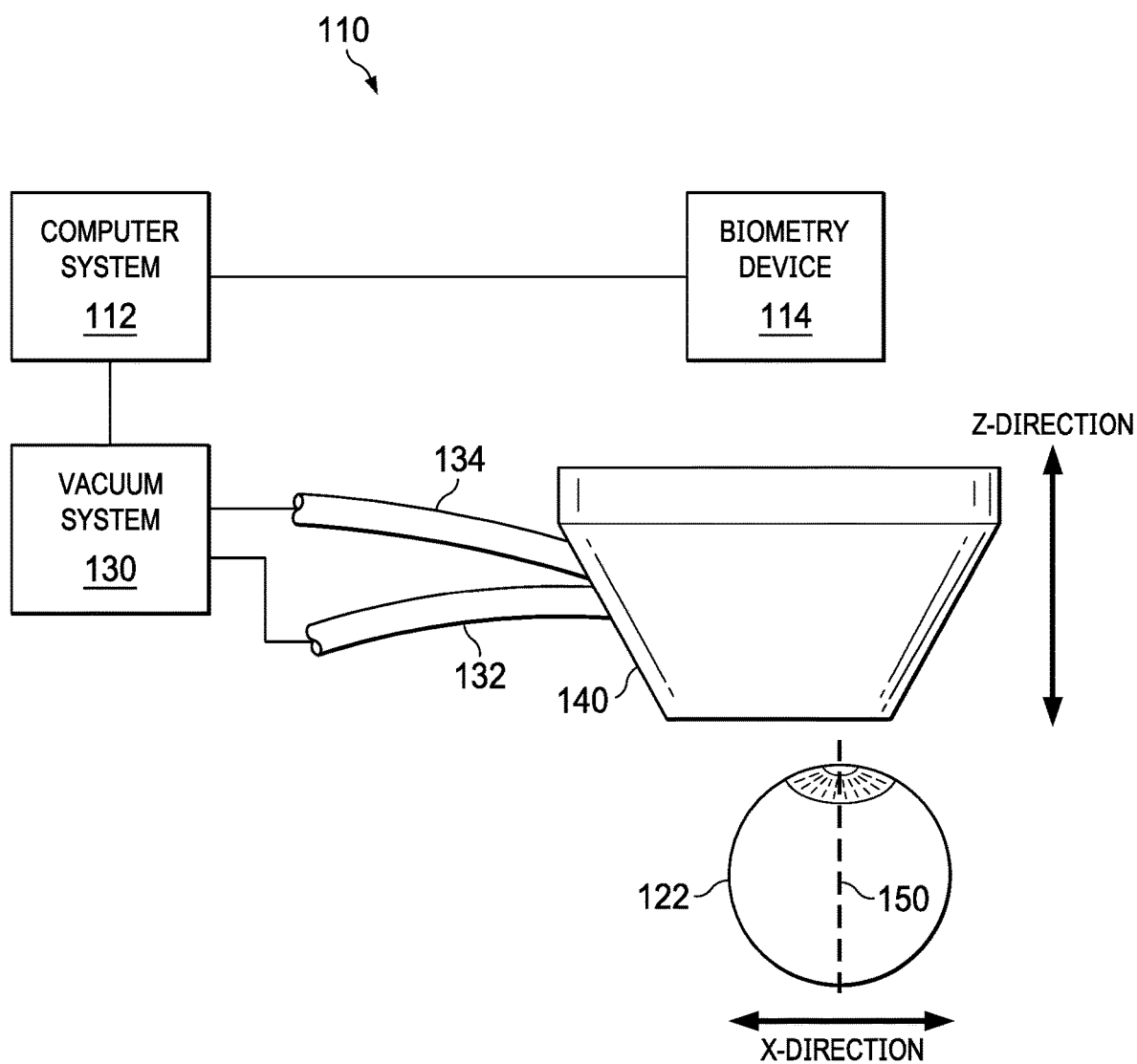
FIG. 1E illustrates an example of a suction ring that is off center in an x-direction.

Turning now to FIG. 1E, an example of a suction ring that is off center in an x-direction is illustrated. As shown, suction ring 140 may be off an optical axis 150 of eye 122, in an x-direction. For example, suction ring 140 may not be properly placed on eye 122 if suction ring 140 is directly lowered in the z-direction.

Figure 1F:
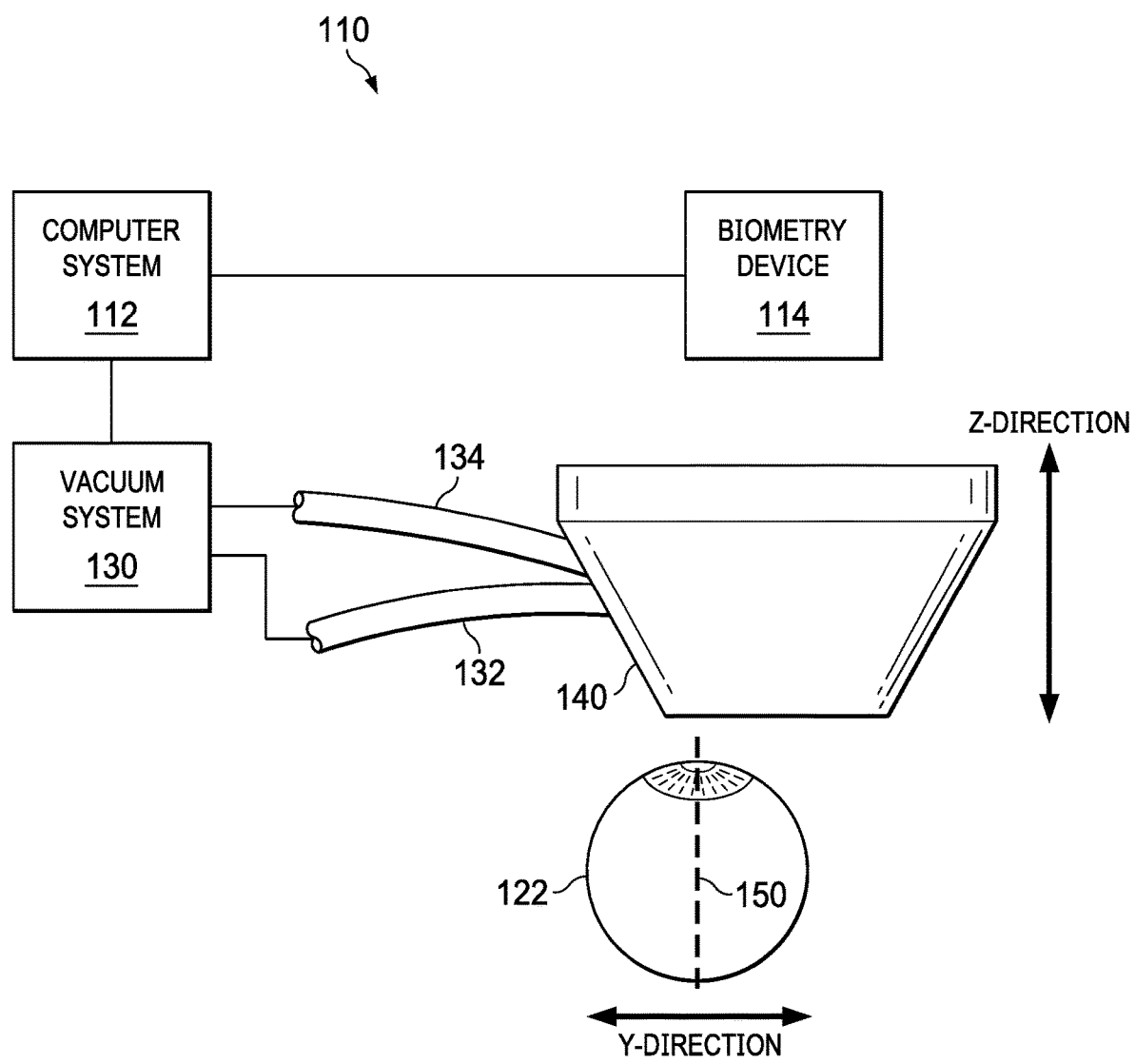
FIG. 1F illustrates an example of a suction ring that is off center in a y-direction.

Turning now to FIG. 1F, an example of a suction ring that is off center in a y-direction is illustrated. As shown, suction ring 140 may be off optical axis 150 of eye 122, in a y-direction. For example, suction ring 140 may not be properly placed on eye 122 if suction ring 140 is directly lowered in the z-direction.

Figure 1G:
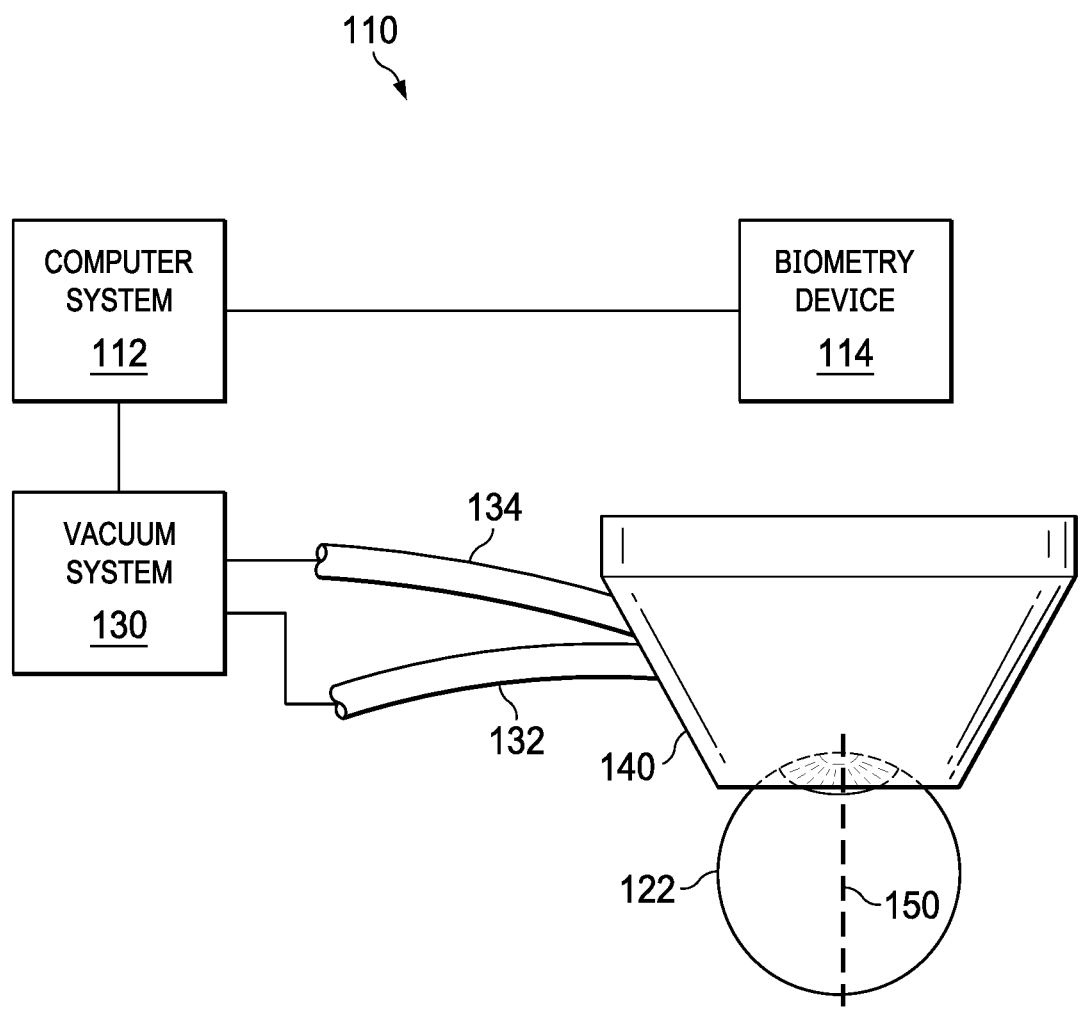
FIG. 1G illustrates an example of a suction ring that is properly placed.

Turning now to FIG. 1G, an example of a suction ring that is properly placed is illustrated. As shown, suction ring 140 may be properly placed on eye 122. For example, suction ring 140 may be properly placed on eye 122 with respect to optical axis 150. As illustrated, suction ring 140 may be docked with eye 122.

Figure 1H:
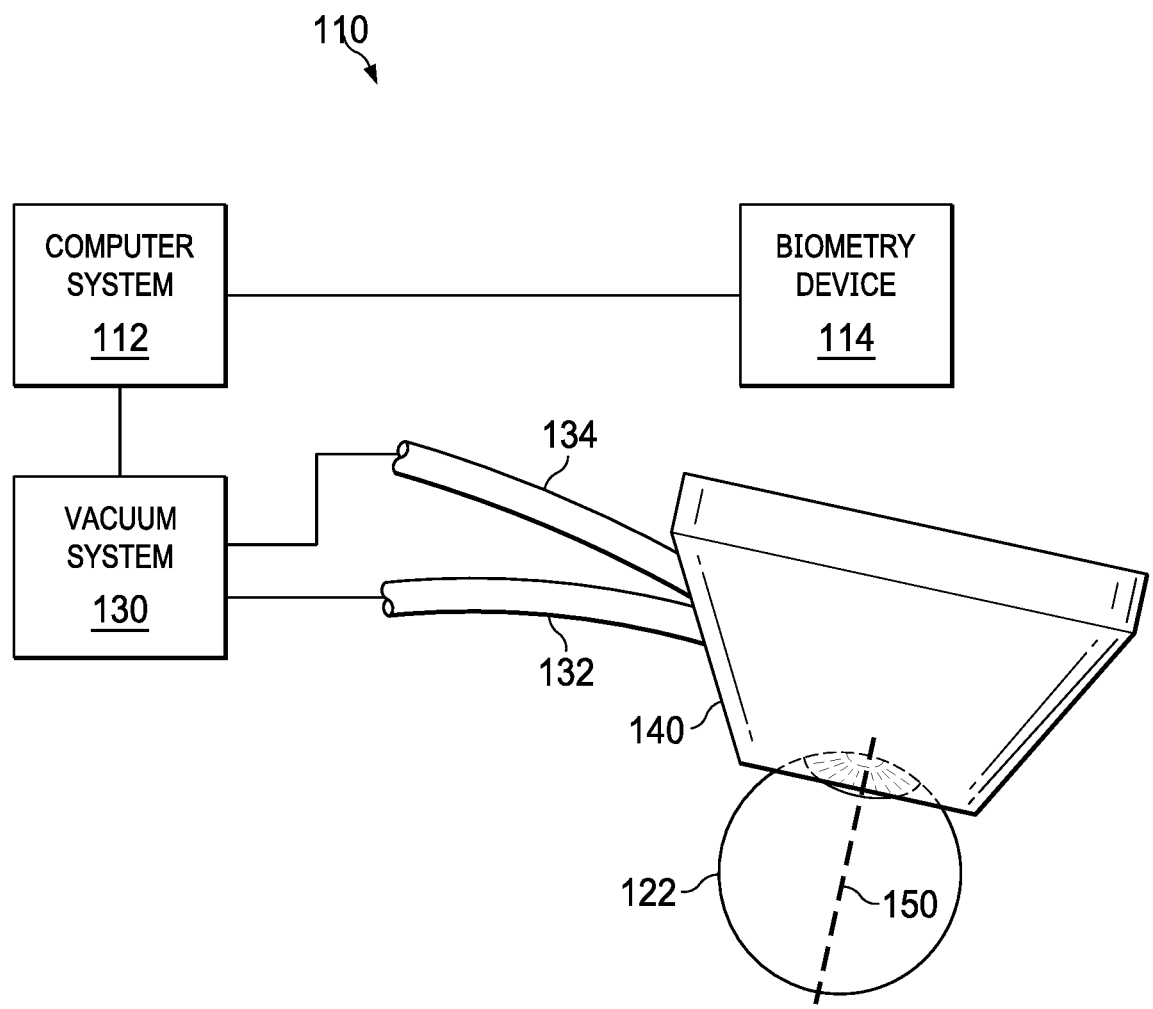
FIG. 1H illustrates another example of a suction ring that is properly placed.

Turning now to FIG. 1H, another example of a suction ring that is properly placed is illustrated. As shown, suction ring 140 may be properly placed on eye 122. In one example, eye 122 may be tilted in an x-direction. In another example, eye 122 may be tilted in a y-direction. Suction ring 140 may be properly placed on eye 122, even though eye 122 may be tilted in the x-direction and/or may be tilted in the y-direction. For example, suction ring 140 may be properly placed on eye 122 when suction ring 140 is placed with respect to optical axis 150, as illustrated. As shown, suction ring 140 may be docked with eye 122.

Figure 1I:
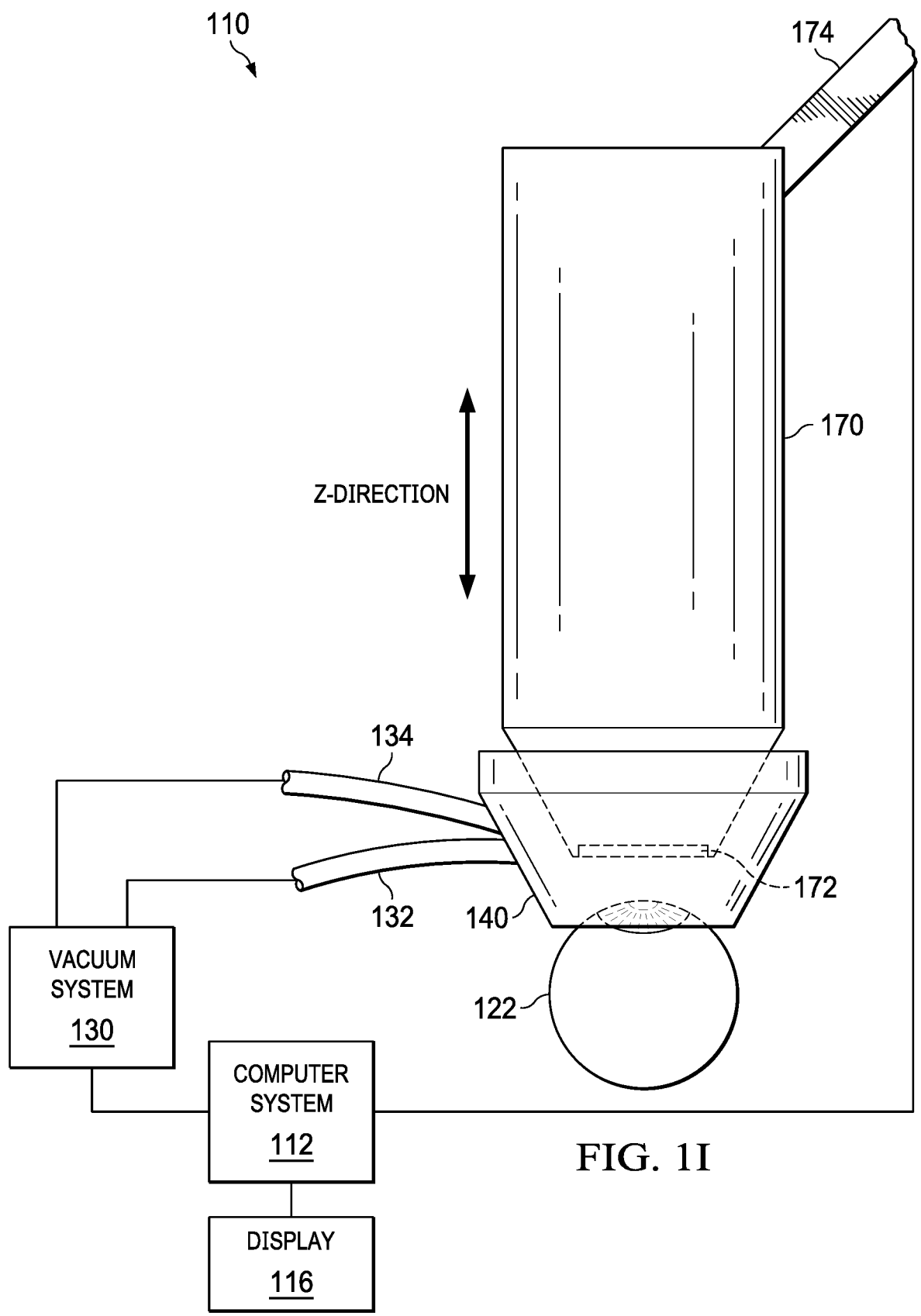
FIG. 1I illustrates a second example of a medical system.

Turning now to FIG. 1I, a second example of a medical system is illustrated. As shown, medical system 110 may include a suction cone 170. For example, suction cone 170 may be or include an aplenation cone. As illustrated, computer system 112 may be coupled to control device 174 of suction cone 170. For example, computer system 112 may control suction cone 170 via control device 174. After suction ring 140 is docked with eye 122, suction cone 170 may be docked with suction ring 140. As illustrated, suction cone 170 may include a lens 172. Although lens 172 is illustrated as flat or planar, lens 172 may include concave shape and/or may include convex shape.

Figure 1J:
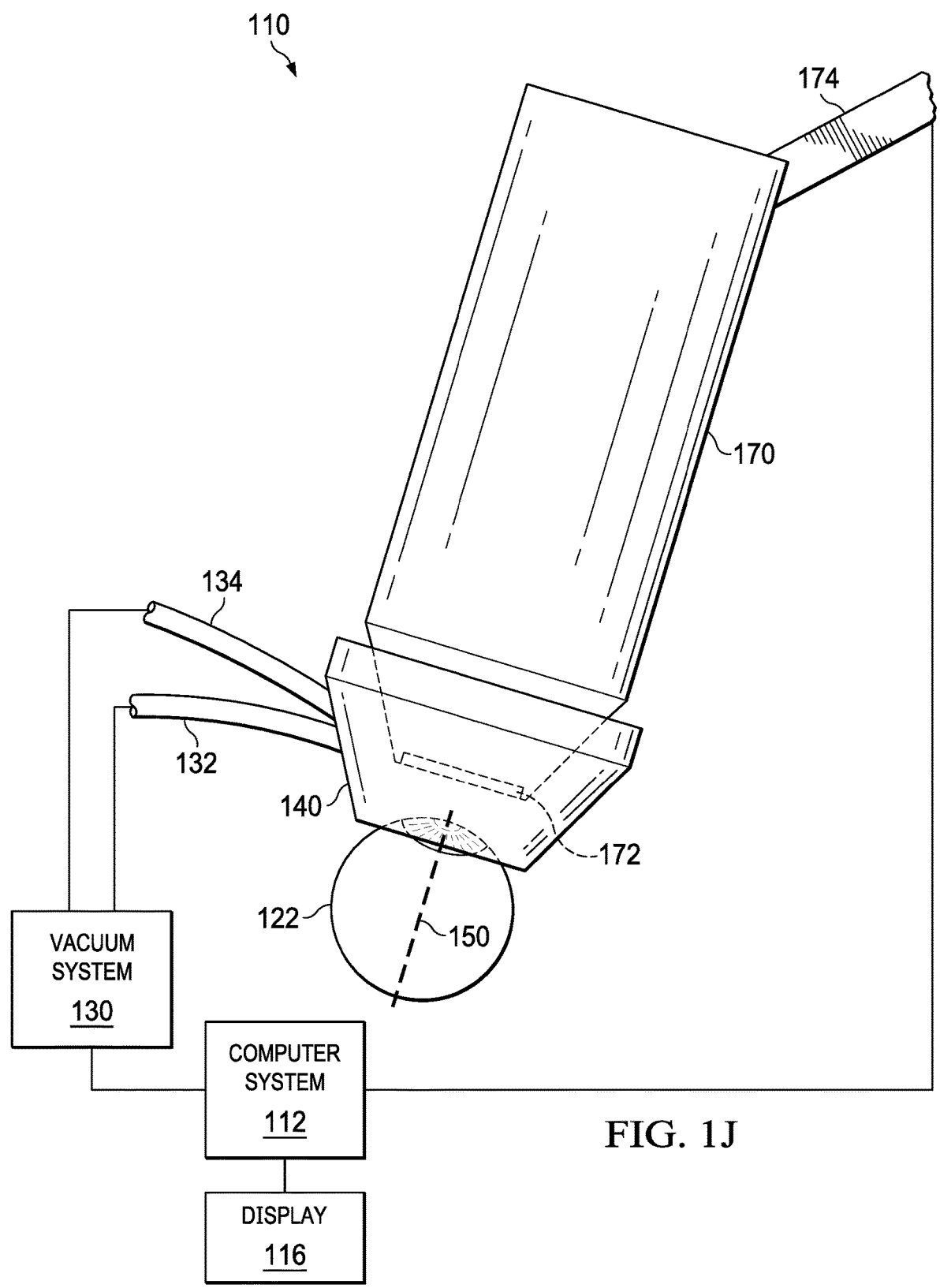
FIG. 1J illustrates an example of a suction ring and a suction cone that are tilted and properly placed.

Turning now to FIG. 1J, an example of a suction ring and a suction cone that are tilted and properly placed is illustrated. As shown, suction ring 140 may be properly placed on eye 122. In one example, eye 122 may be tilted in an x-direction. In another example, eye 122 may be tilted in a y-direction. Suction ring 140 may be properly placed on eye 122, even though eye 122 may be tilted in the x-direction and/or may be tilted in the y-direction. For example, suction ring 140 may be properly placed on eye 122 when suction ring 140 is placed with respect to optical axis 150, as illustrated. As shown, suction ring 140 may be docked with eye 122. As illustrated, suction cone 170 may be docked with suction ring 140, such that both suction ring 140 and suction cone 170 are aligned with optical axis 150.

Figure 2A:
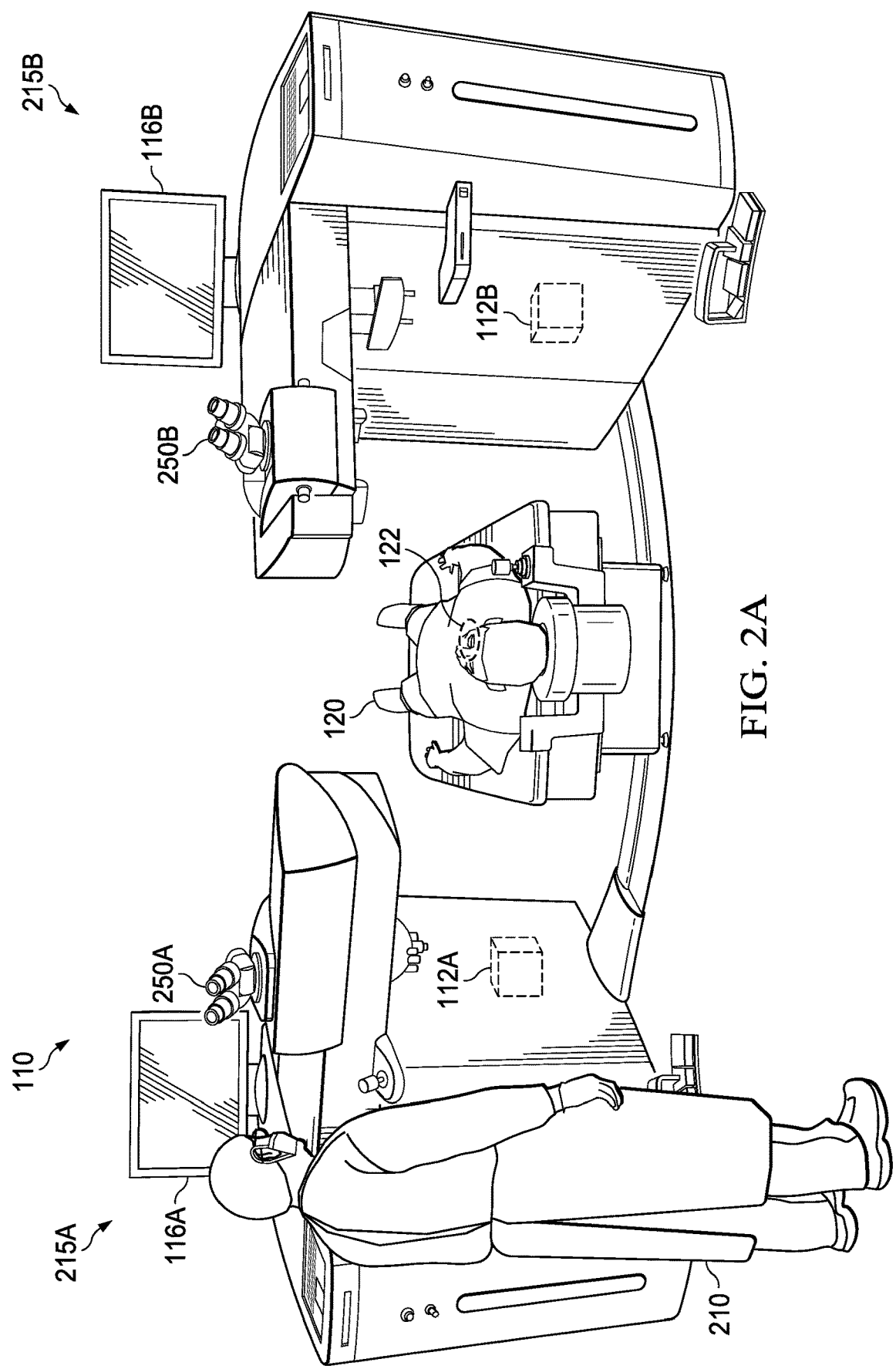
FIG. 2A illustrates another example of a medical system.

Turning now to FIG. 2A, another example of a medical system is illustrated. As shown, a surgeon 210 may utilize medical system 110. For example, surgeon 210 may utilize system 110 in a surgery involving eye 122 of a patient 120. System 110 may include multiple systems. As shown, system 110 may include a cutting system 215A. For example, surgeon 210 may utilize system 215A in cutting eye 122. Eye 122 may include a flap in a cornea of an eye of patient 120. As illustrated, system 110 may include a shaping system 215B. For example, surgeon 210 may utilize shaping system 215B in performing ablation on an interior part of the cornea of patient 120.

As shown, system 215A may include a display 116A. As illustrated, system 215A may include a microscope display 250A. For example, microscope display 250A may include a microscope integrated display (MID). System 215A may include one or more of image sensors 160A-160C, one or more of light projectors 162A-162C, one or more of depth sensors 164A-164C, OLCR device 166, and/or wavefront device 168, among others. System 215A may include one or more of suction ring 150, suction cone 170, and vacuum system 130, among others. As illustrated, system 215B may include a display 116B. As shown, system 215B may include a microscope display 250B. For example, microscope display 250B may include a MID. System 215B may include one or more of image sensors 160A-160C, one or more of light projectors 162A-162C, one or more of depth sensors 164A-164C, OLCR device 166, and/or wavefront device 168, among others.

System 215A may include a laser, such as a femtosecond laser, which may use short laser pulses to ablate a series of small portions of corneal tissue to form a flap that may be lifted up to expose an interior part of the cornea. The flap may be planned and cut using one or both of cutting device displays 116A and 250A, along with control devices and a computer system 112A. As shown, system 215A may include computer system 112A. For example, computer system 112A may be coupled to one or more of image sensors 160A-160C, one or more of light projectors 162A-162C, one or more of depth sensors 164A-164C, OLCR device 166, and/or wavefront device 168, among others, of system 215A. As illustrated, system 215B may include computer system 112B. For example, computer system 112B may be coupled to one or more of image sensors 160A-160C, one or more of light projectors 162A-162C, one or more of depth sensors 164A-164C, OLCR device 166, and/or wavefront device 168, among others, of system 215B.

Figure 2B:
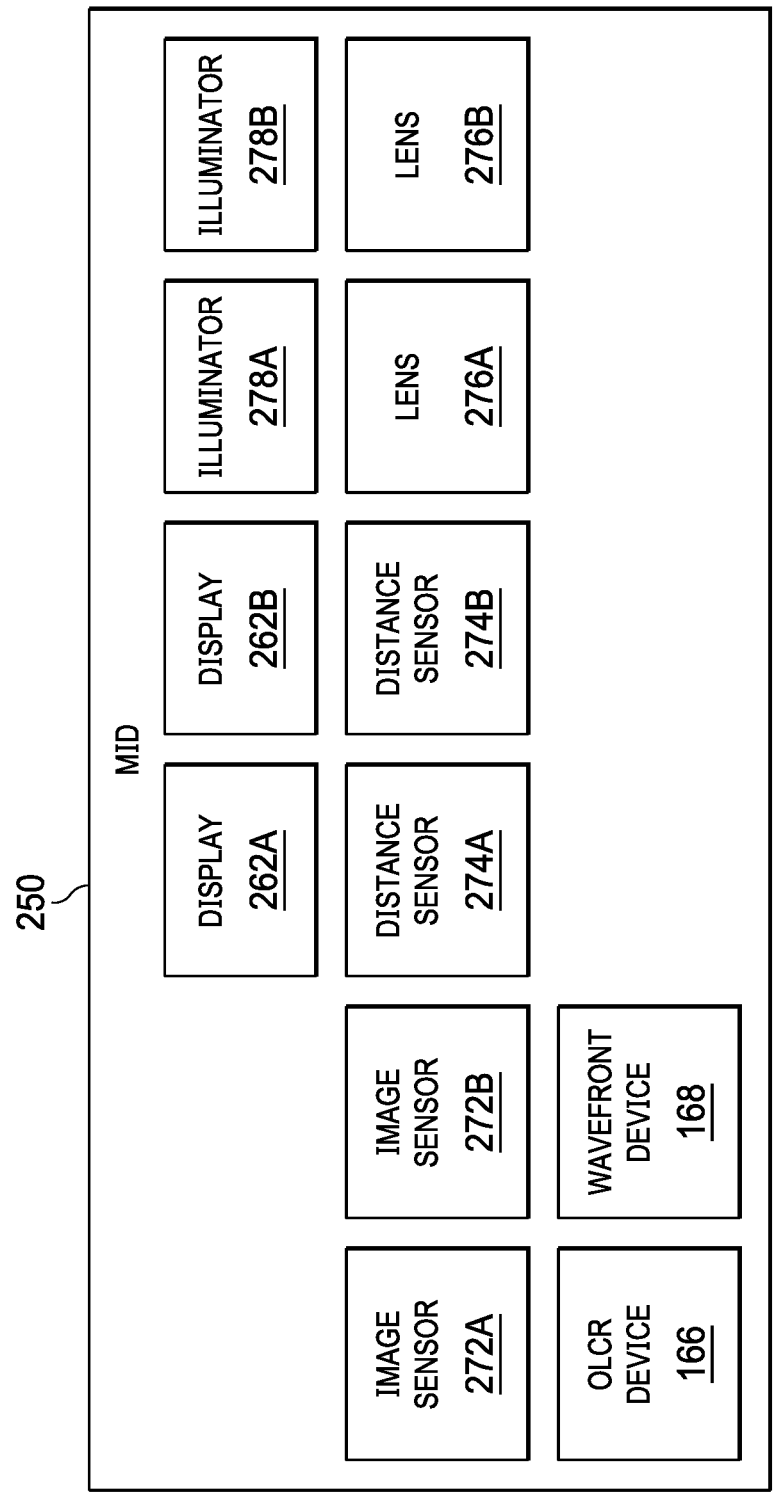
FIG. 2B illustrates an example of a microscope integrated display.

Systems 215A and 215B may be physically separated as shown in FIG. 2B. Patient 120 may be moved between systems 215A and 215B. Alternatively, patient 120 may remain stationary and systems 215A and 215B may be moved to patient 120. Systems 215A and 215B may be physically combined into a single unitary device, such that neither the device nor patient 120 is repositioned when switching between systems 215A and 215B.

System 110 may include one or more control devices for controlling systems 215A and 215B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 110 may include at least one computer system configured to generate an image presented on at least one of displays 116A, 250A, 116B, and 250B, among others. For example, the at least one computer system may include one or more of computer systems 112A and 112B. One or more of computer systems 112A and 112B may be coupled to observational devices, such as a microscope, a camera, an optical coherence tomography (OCT) device or display, or another device able to measure the position of the eye undergoing surgery. One or more of computer systems 112A and 112B may be coupled to one or more of the control devices.

In one example, cutting device computer system 112A: i) may be coupled to observational devices that observe eye 122 when patient 120 is positioned with system 215A, ii) may provide graphical information regarding the planned flap location and the planned area of ablation to one or more of displays 116A and 250A, and iii) may be coupled to one or more control devices of system 215A. In a second example, shaping device computer 112B: i) may be coupled to observational devices that observe eye 122 when patient 120 is positioned with a shaping device, ii) may provide graphical information regarding the planned flap location and the planned area of ablation to one or more of displays 1160B and 250B, and iii) may be coupled to one or more control devices of system 215B. In another example, a computer system may include the properties and/or the attributes described above with respect to computer systems 112A and 112B.

A computer system of a system 110 may be coupled to another part of system 110 in a wired fashion or in a wireless fashion. Data of one or more computer systems of system 110 may be stored in a database, stored locally, stored via a remote computer system, and/or stored via remote data center, that store patient data, treatments plans, and/or other information associated with medical treatments and/or system 110. In one example, the database may include a relational database. In a second example, the database may include a graph database. In another example, the database may include a "Not Only SQL" (NoSQL) database.

System 110 may enter information regarding a patient and the treatment to be performed on that patient or actually performed on that patient. System 110 may allow a user to enter and view information regarding a patient and the treatment to be performed on that patient. Such data may include information about the patient, such as identifying information, the patient's medical history, and/or information about eye 122 being treated, among others. Such data may include information about the treatment plans, such as the shape and location of a corneal cut, a shape, and/or location of ablation, among others.

Turning now to FIG. 2B, an example of a microscope integrated display is illustrated. As shown, MID 250 may include displays 262A and 262B. For example, surgeon 210 may look into multiple eye pieces, and displays 262A and 262B may display information to surgeon 210. Although MID 250 is shown with multiple displays, MID 250 may include a single display 262. For example, MID 250 may be implemented with one or more displays 262. A display 262 may display any image and/or any information that display 116 may display. As shown, MID 250 may include image sensors 272A and 272B. In one example, image sensors 272A and 272B may acquire images. In a second example, image sensors 272A and 272B may include cameras. In another example, an image sensor 272 may acquire images via one or more of visible light, infrared light, and ultraviolet light, among others. One or more image sensors 272A and 272B may provide data of images to computer system 112. Although MID 250 is shown with multiple image sensors, MID 250 may include a single image sensor 272. For example, MID 250 may be implemented with one or more image sensors 272.

As illustrated, MID 250 may include distance sensors 274A and 274. For example, a distance sensor 274 may determine a distance to surgical tooling equipment 220. Distance sensor 274 may determine a distance associated with a z-axis. Although MID 250 is shown with multiple image sensors, MID 250 may include a single distance sensor 274. In one example, MID 250 may be implemented with one or more distance sensors 274. In another example, MID 250 may be implemented with no distance sensor. As shown, MID 250 may include lenses 276A and 276B. Although MID 250 is shown with multiple lenses 276A and 276B, MID 250 may include a single lens 276. For example, MID 250 may be implemented with one or more lenses 276. As illustrated, MID 250 may include illuminators 278A and 278B. For example, an illuminator 278 may provide and/or produce one or more of visible light, infrared light, and ultraviolet light, among others. Although MID 250 is shown with multiple illuminators, MID 250 may include a single illuminator 278. For example, MID 250 may be implemented with one or more illuminators 278.

An illuminator 278 may provide infrared light. Computer system 112 may receive image data, based at least on the infrared light reflected. For example, image sensor 272 may receive reflected infrared light and may provide data, based at least on the reflected infrared light, to computer system 112. An illuminator 278 may provide white light. Computer system 112 may receive image data, based at least on the white light reflected. For example, image sensor 272 may receive reflected white light and may provide data, based at least on the reflected white light, to computer system 112. An illuminator 278 may provide ultraviolet light. Computer system 112 may receive image data, based at least on the ultraviolet light reflected. For example, image sensor 272 may receive reflected ultraviolet light and may provide data, based at least on the reflected ultraviolet light, to computer system 112. MID 250 may include one or more structures and/or one or more functionalities as those described with reference to biometry device 114. In one example, MID 250 may include OLCR device 166. In another example, MID 250 may include wavefront device 168.

As an example, surgical tooling equipment may be marked with one or more patterns. The one or more patterns may be utilized in identifying the surgical tooling equipment. The one or more patterns may include one or more of a hash pattern, a stripe pattern, and a fractal pattern, among others. As another example, the surgical tooling equipment may be marked with a dye and/or a paint. The dye and/or the paint may reflect one or more of visible light, infrared light, and ultraviolet light, among others. In one example, an illuminator 278 may provide ultraviolet light, and image sensor 272 may receive the ultraviolet light reflected from the surgical tooling equipment. Computer system 112 may receive image data, based at least on the ultraviolet light reflected from the surgical tooling equipment, from image sensor 272 and may utilize the image data, based at least on the ultraviolet light reflected from the surgical tooling equipment, to identify the surgical tooling equipment from other image data provided by image sensor 272. In another example, an illuminator 278 may provide infrared light, and image sensor 272 may receive the infrared light reflected from the surgical tooling equipment. Computer system 112 may receive image data, based at least on the infrared light reflected from the surgical tooling equipment, from image sensor 272 and may utilize the image data, based at least on the infrared light reflected from the surgical tooling equipment, to identify the surgical tooling equipment from other image data provided by image sensor 272.

Figure 3A:
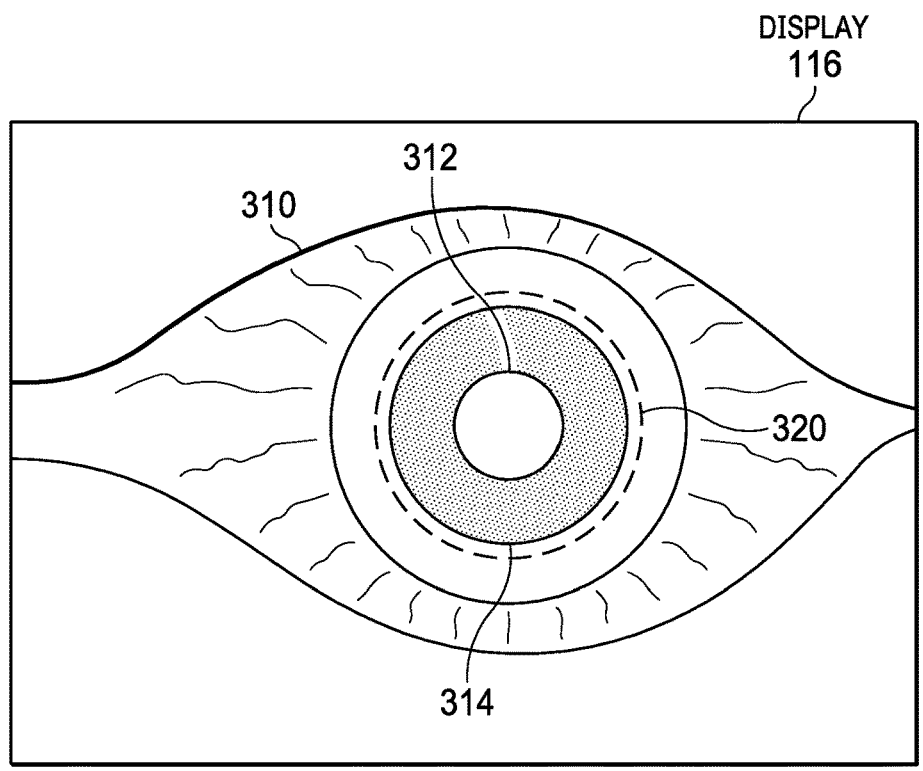
FIG. 3A illustrates an example of an overlay of an iris of an eye.

Turning now to FIG. 3A, an example of an overlay of an iris of an eye is illustrated. As shown, display 116 may display an image 310 of eye 122. System 110 may determine an image 314 of an iris of eye 122. As illustrated, display 116 may display an overlay 320. For example, overlay 320 may mark an outer boundary of image 314 of the iris of eye 122. Overlay 320 may be centered with respect to an image 312 of a pupil of eye 122. System 110 may determine overlay 320 via one or more of a computer vision method, a computer vision process, and a computer vision system, among others. One or more positions of overlay 320 may be changed and/or updated based at least on one or more movements of eye 122.

Figure 3B:
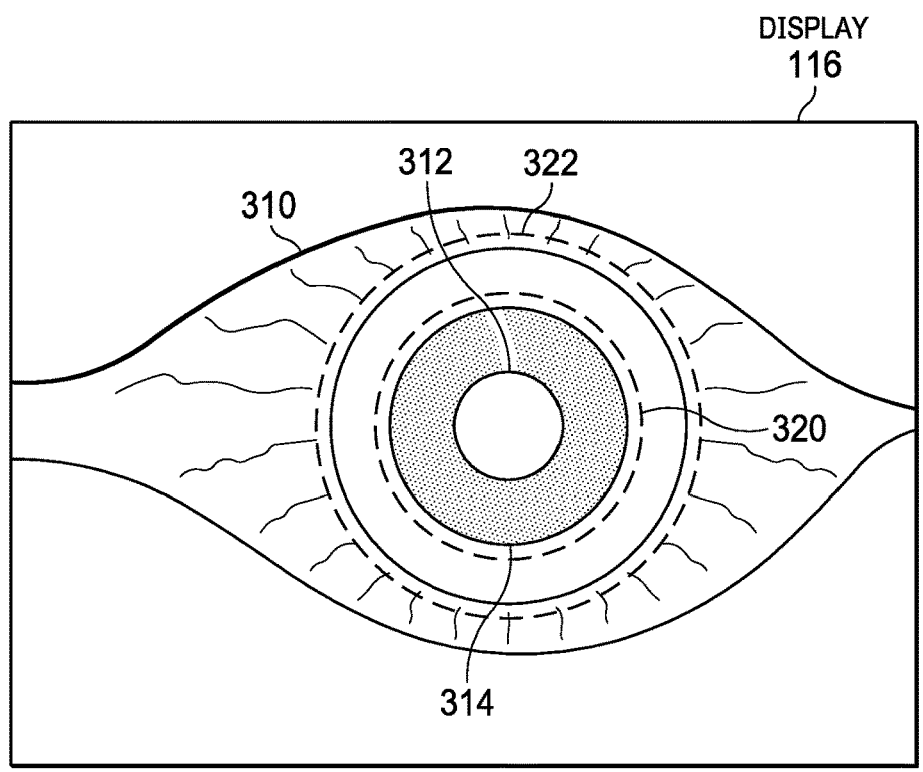
FIG. 3B illustrates a second example of an overlay of an eye.

Turning now to FIG. 3B, a second example of an overlay of an eye is illustrated. As shown, an overlay 322 may surround overlay 320. For example, overlay 322 may augment overlay 320. One or more positions of overlay 322 may be changed and/or updated based at least on one or more movements of eye 122.

Figure 3C:
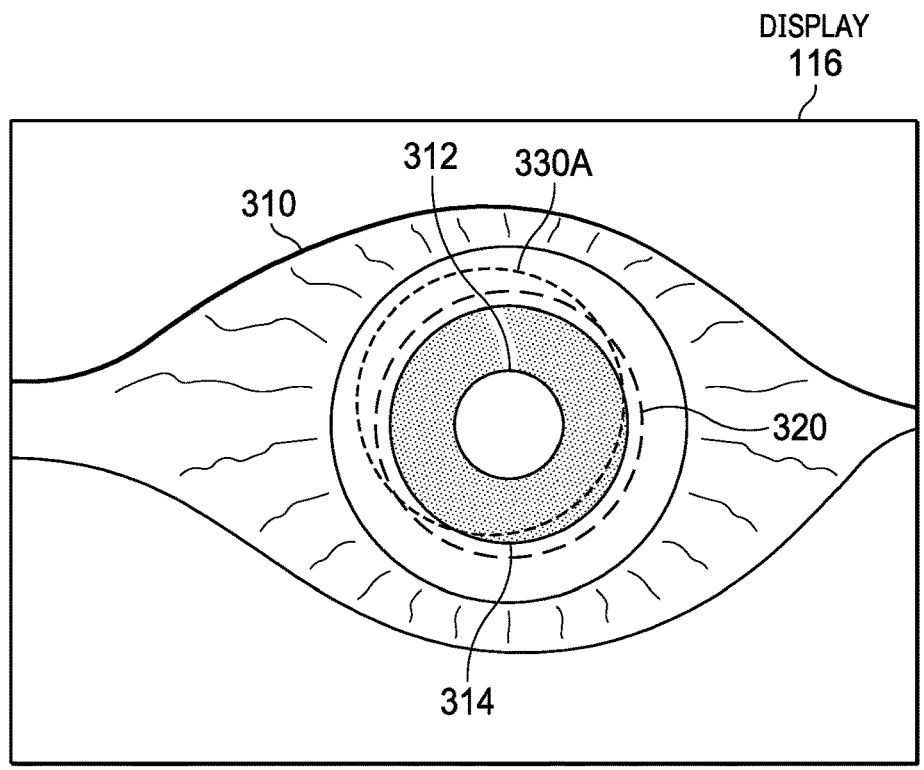
FIG. 3C illustrates a third example of an overlay of an eye.

Turning now to FIG. 3C, a third example of an overlay of an eye is illustrated. As shown, display 116 may display an overlay 330A. For example, overlay 330A may represent an alignment of suction ring 140. Overlay 330A may represent an alignment of suction ring 140 if suction ring 140 was moved in a z-direction to eye 122. As illustrated, overlay 330A indicates that suction ring 140 may not be properly aligned. In one example, eye 122 may be tilted in an x-direction, as illustrated in FIG. 1C. In another example, suction ring 140 may be off optical axis 150 of eye 122 in an x-direction, as illustrated in FIG. 1E. One or more positions of overlay 330A may be changed and/or updated based at least on one or more movements of suction ring 140.

Figure 3D:
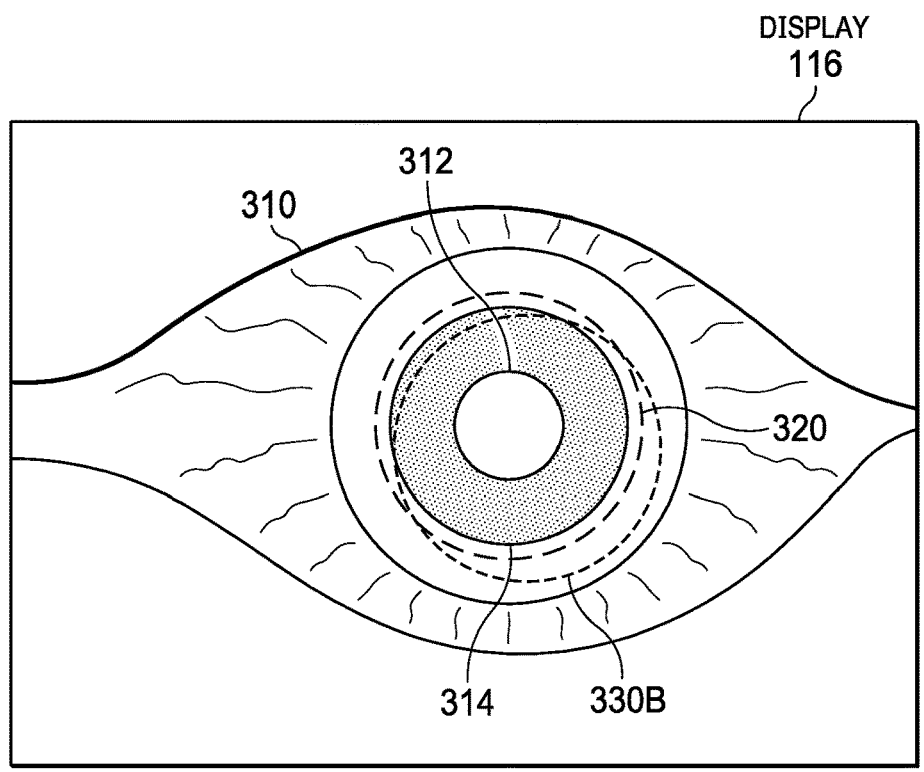
FIG. 3D illustrates a fourth example of an overlay of an eye.

Turning now to FIG. 3D, a fourth example of an overlay of an eye is illustrated. As shown, display 116 may display an overlay 330B. For example, overlay 330B may represent an alignment of suction ring 140. Overlay 330B may represent an alignment of suction ring 140 if suction ring 140 was moved in a z-direction to eye 122. As illustrated, overlay 330B indicates that suction ring 140 may not be properly aligned. In one example, eye 122 may be tilted in a y-direction, as illustrated in FIG. 1D. In another example, suction ring 140 may be off optical axis 150 of eye 122 in a y-direction, as illustrated in FIG. 1F. One or more positions of overlay 330B may be changed and/or updated based at least on one or more movements of suction ring 140.

Figure 3E:
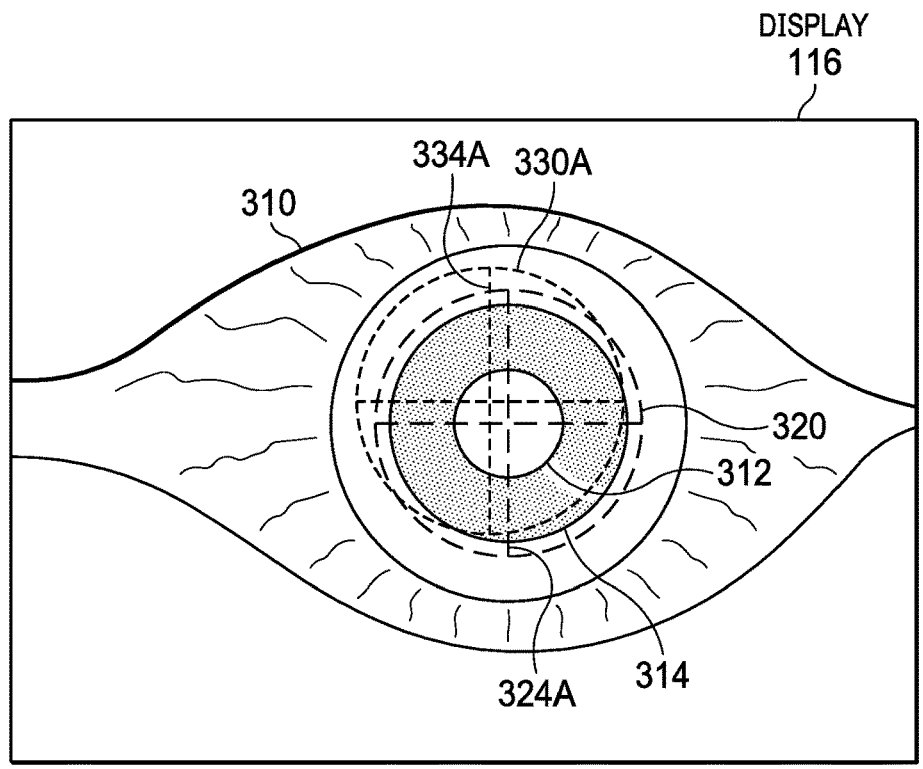
FIG. 3E illustrates a fifth example of an overlay of an eye.

Turning now to FIG. 3E, a fifth example of an overlay of an eye is illustrated. As shown, display 116 may display an overlay 324A. For example, overlay 324A may be aligned with one or more of image 312 of the pupil of eye 122 and image 314 of the iris of eye 122, among others. Overlay 324A may be aligned with a center of image 312 of the pupil of eye 122. Overlay 324A may be aligned with one or more structures of image 314 of the iris of eye 122. Overlay 324A may convey and/or guide a placement and/or a position of suction ring 140.

As shown, display 116 may display an overlay 334A. For example, overlay 334A may represent an alignment of suction ring 140. Overlay 334A may represent an alignment of suction ring 140 if suction ring 140 was moved in a z-direction to eye 122. For example, overlay 334A may represent a reticle (e.g., crosshairs). As illustrated, overlay 334A indicates that suction ring 140 may not be properly aligned. In one example, eye 122 may be tilted in an x-direction, as illustrated in FIG. 1C. In a second example, eye 122 may be tilted in a y-direction, as illustrated in FIG. 1D. In a third example, suction ring 140 may be off optical axis 150 of eye 122 in an x-direction, as illustrated in FIG. 1E. In another example, suction ring 140 may be off optical axis 150 of eye 122 in a y-direction, as illustrated in FIG. 1F. One or more positions of overlay 324A may be changed and/or updated based at least on one or more movements of eye 122. One or more positions of overlay 334A may be changed and/or updated based at least on one or more movements of suction ring 140.

Figure 3F:
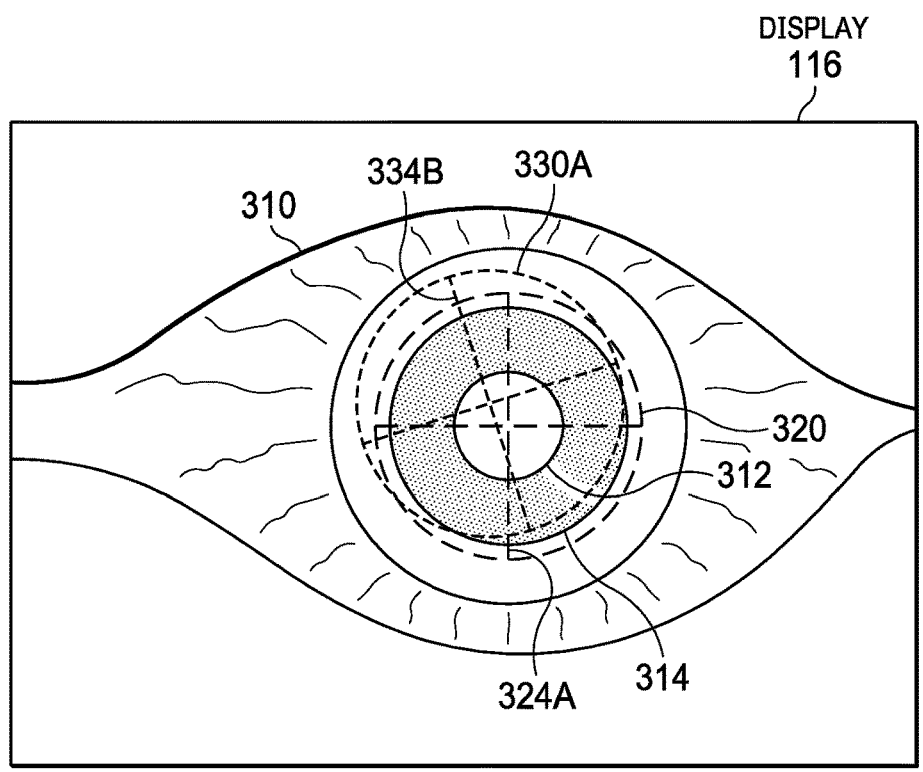
FIG. 3F illustrates a sixth example of an overlay of an eye.

Turning now to FIG. 3F, a sixth example of an overlay of an eye is illustrated. As shown, display 116 may display overlay 324A. For example, overlay 324A may be aligned with one or more image of 312 of the pupil of eye 122 and image 314 of the iris of eye 122, among others. Overlay 324A may be aligned with a center of image 312 of the pupil of eye 122. Overlay 324A may be aligned with one or more structures of image 314 of the iris of eye 122. Overlay 324A may convey and/or guide a placement and/or a position of suction ring 140.

As shown, display 116 may display an overlay 334B. For example, overlay 334B may represent an alignment of suction ring 140. Overlay 334B may represent an alignment of suction ring 140 if suction ring 140 was moved in a z-direction to eye 122. For example, overlay 334B may represent a reticle (e.g., crosshairs). As illustrated, overlay 334B indicates that suction ring 140 may not be properly aligned. In one example, eye 122 may be tilted in an x-direction, as illustrated in FIG. 1C. In a second example, eye 122 may be tilted in a y-direction, as illustrated in FIG. 1D. In a third example, suction ring 140 may be off optical axis 150 of eye 122 in an x-direction, as illustrated in FIG. 1E. In a fourth example, suction ring 140 may be off optical axis 150 of eye 122 in a y-direction, as illustrated in FIG. 1F. In another example, suction ring 140 may be rotated. One or more positions of overlay 324A may be changed and/or updated based at least on one or more movements of eye 122. One or more positions of overlay 334B may be changed and/or updated based at least on one or more movements of suction ring 140.

Figure 3G:
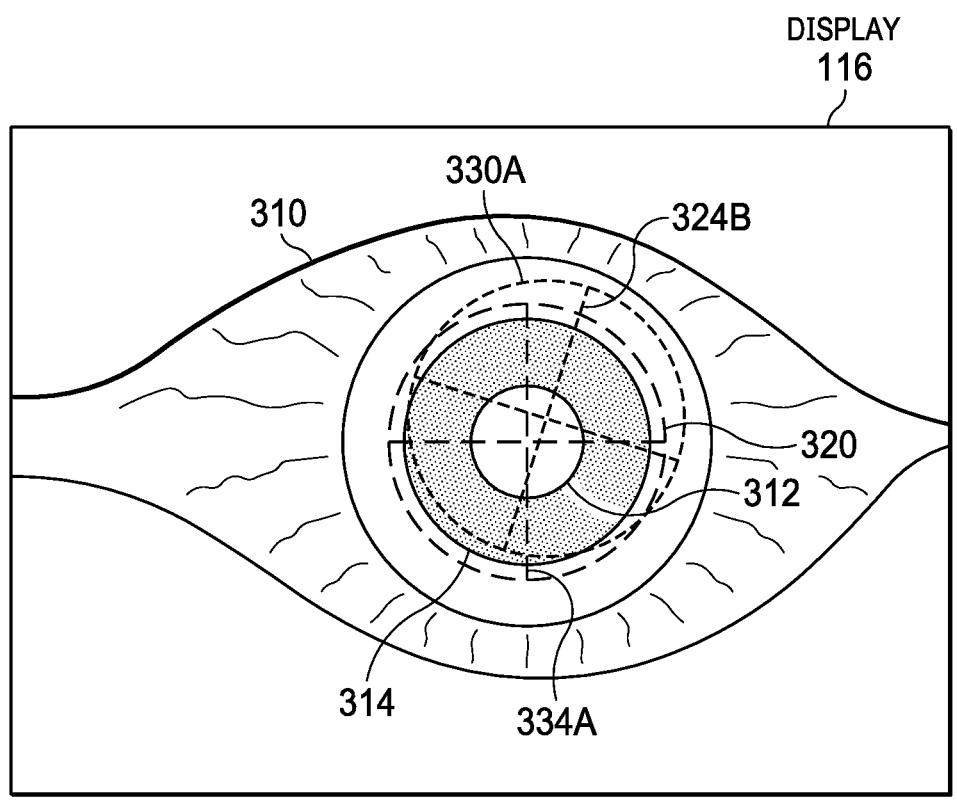
FIG. 3G illustrates another example of an overlay of an eye.

Turning now to FIG. 3G, another example of an overlay of an eye is illustrated. As shown, display 116 may display an overlay 324B. For example, overlay 324B may be aligned with one or more image of 312 of the pupil of eye 122 and image 314 of the iris of eye 122, among others. Overlay 324B may be aligned with a center of image 312 of the pupil of eye 122. Overlay 324B may be aligned with one or more structures of image 314 of the iris of eye 122. Overlay 324B may convey and/or guide a placement and/or a position of suction ring 140.

Eye 122 may rotate about optical axis 150. In one example, eye 122 may exhibit torsional movement. In another example, eye 122 may exhibit cyclorotation. Overlay 324B may indicate one or more rotations of eye 122. For example, overlay 324B may indicate one or more rotations of eye 122 about optical axis 150. Overlay 324B may indicate one or more of a rotation of eye 122 about optical axis 150, a tilt of eye 122 in an x-direction, and a tilt of eye 122 in a y-direction, among others.

As shown, display 116 may display an overlay 334A. For example, overlay 334A may represent an alignment of suction ring 140. Overlay 334A may represent an alignment of suction ring 140 if suction ring 140 was moved in a z-direction to eye 122. For example, overlay 334A may represent a reticle (e.g., crosshairs). As illustrated, overlay 334A indicates that suction ring 140 may not be properly aligned. In one example, eye 122 may be tilted in an x-direction, as illustrated in FIG. 1C. In a second example, eye 122 may be tilted in a y-direction, as illustrated in FIG. 1D. In a third example, suction ring 140 may be off optical axis 150 of eye 122 in an x-direction, as illustrated in FIG. 1E. In a fourth example, suction ring 140 may be off optical axis 150 of eye 122 in a y-direction, as illustrated in FIG. 1F. In another example, suction ring 140 may be rotated. One or more positions of overlay 324B may be changed and/or updated based at least on one or more movements of eye 122. One or more positions of overlay 334A may be changed and/or updated based at least on one or more movements of suction ring 140.

Figure 4A:
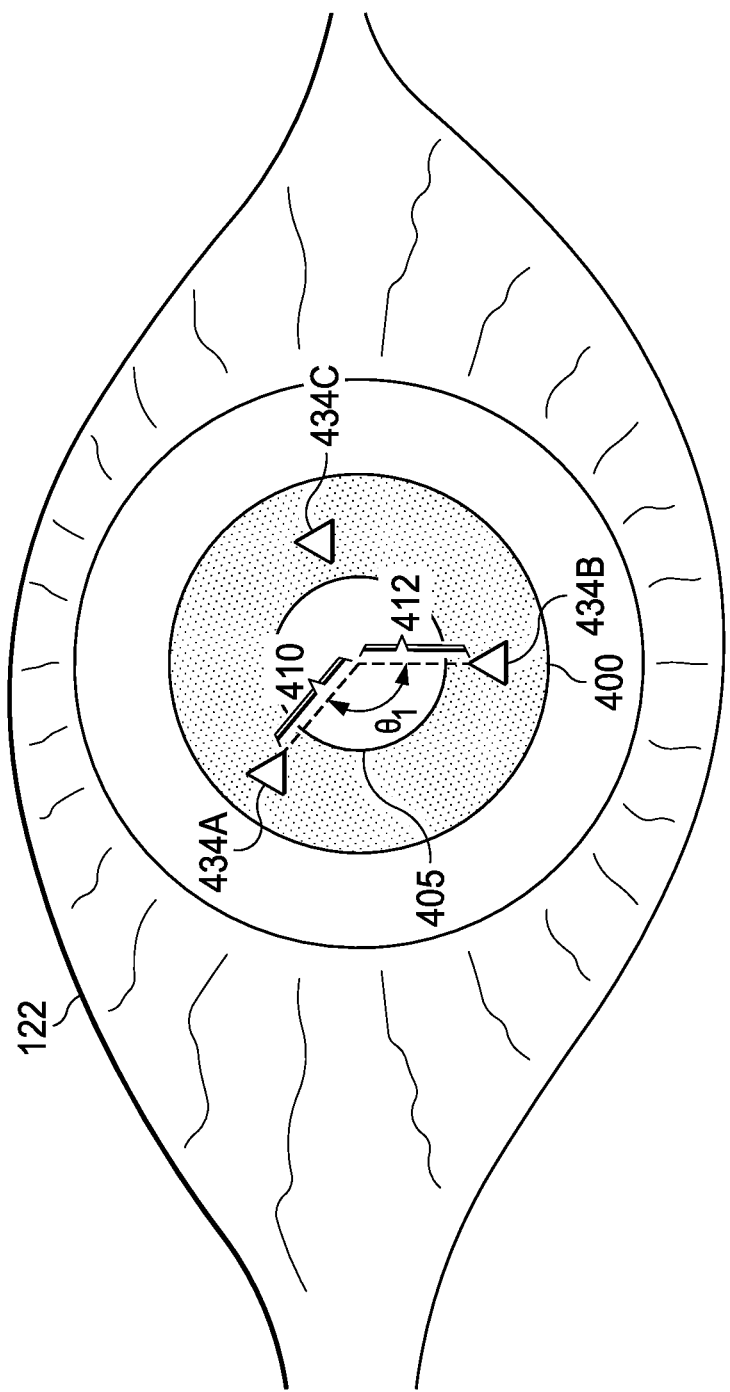
FIGS. 4A and 4B illustrate examples of multiple iris structures.
Figure 4B:
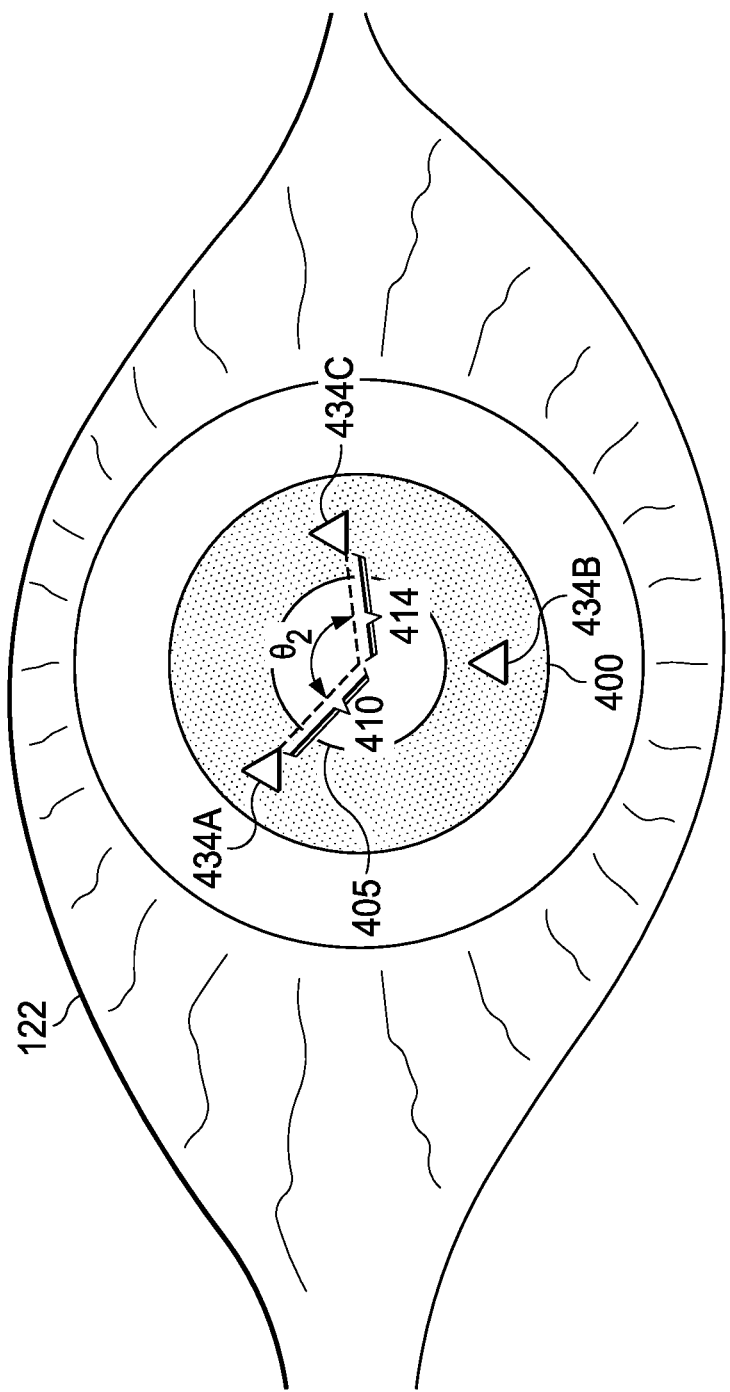

Turning now to FIGS. 4A and 4B, examples of multiple iris structures are illustrated. As shown, an iris 400 of eye 122 may include iris structures 434A-434C. For example, system 110 may determine iris structures 434A-434C. One or more measurements associated with iris structures 434A-434C may be determined. In one example, one or more measurements 410-414 may be determined. In another example, one or more measurements $\theta_1$ and $\theta_2$ may be determined. System 110 may determine one or more measurements 410-414 and/or one or more measurements $\theta_1$ and $\theta_2$, among others. For example, system 110 may determine one or more measurements 410-414 and/or one or more measurements $\theta_1$ and $\theta_2$, among others, with respect to a pupil 405 of eye 122. System 110 may determine one or more measurements 410-414 and/or one or more measurements $\theta_1$ and $\theta_2$, among others, with respect to a center of pupil 405 of eye 122, as illustrated.

One or more of iris structures 434A-434C may be utilized in determining one or more positions of one or more overlays 320, 322, 324A, 324B, 330A, 330B, 334A, and 334B, among others. In one example, system 110 may utilize one or more of iris structures 434A-434C in determining one or more positions of one or more overlays 320, 322, 324A, 324B, 330A, 330B, 334A, and 334B, among others. In another example, system 110 may utilize one or more of iris structures 434A-434C in determining one or more measurements 410-414 and/or one or more measurements $\theta_1$ and $\theta_2$, among others. One or more positions of respective one or more iris structures 434A-434C may be utilized as respective one or more reference positions in determining one or more positions of one or more overlays 320, 322, 324A, 324B, 330A, 330B, 334A, and 334B, among others.

As illustrated, measurement 410 may include a distance measurement from the center of pupil 405 to iris structure 434A. As shown, measurement 412 may include a distance measurement from the center of pupil 405 to iris structure 434B. As illustrated, measurement 414 may include a distance measurement from the center of pupil 405 to iris structure 434C. As shown, $\theta_1$ may include an angular measurement from iris structure 434A and iris structure 434B, with respect to the center of pupil 405. For example, $\theta_1$ may include an angular measurement between iris structure 434A and iris structure 434B, with respect to the center of pupil 405. As illustrated, $\theta_2$ may include an angular measurement from iris structure 434A and iris structure 434C, with respect to the center of pupil 405. For example, $\theta_2$ may include an angular measurement between iris structure 434A and iris structure 434C, with respect to the center of pupil 405. System 110 may utilize one or more of measurements 410-414 and/or one or more measurements $\theta_1$ and $\theta_2$, among others, in determining one or more positions of one or more overlays 320, 322, 324A, 324B, 330A, 330B, 334A, and 334B, among others.

Figure 4C:
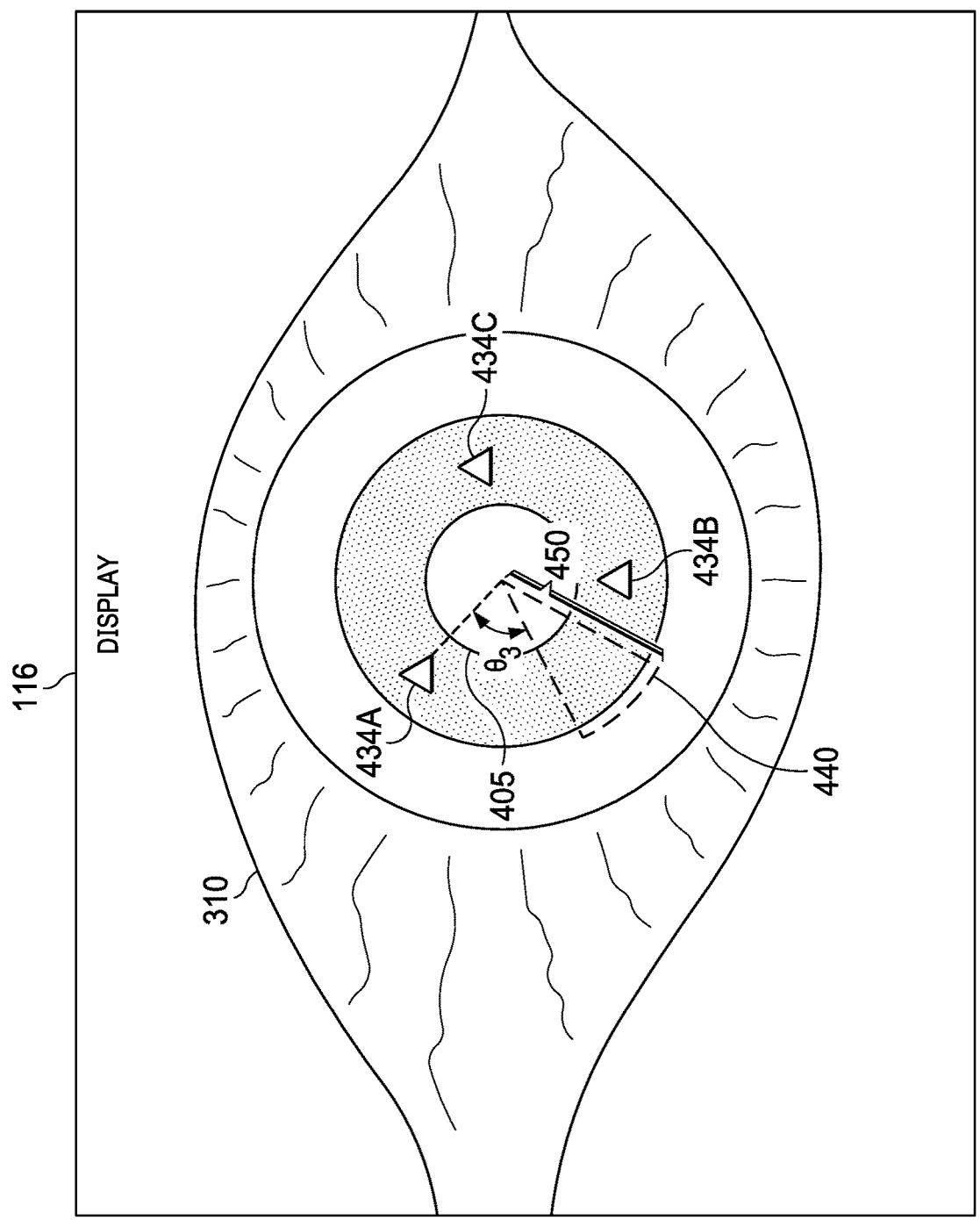
FIGS. 4C-4E illustrate examples of indicating incision sites.
Figure 4D:
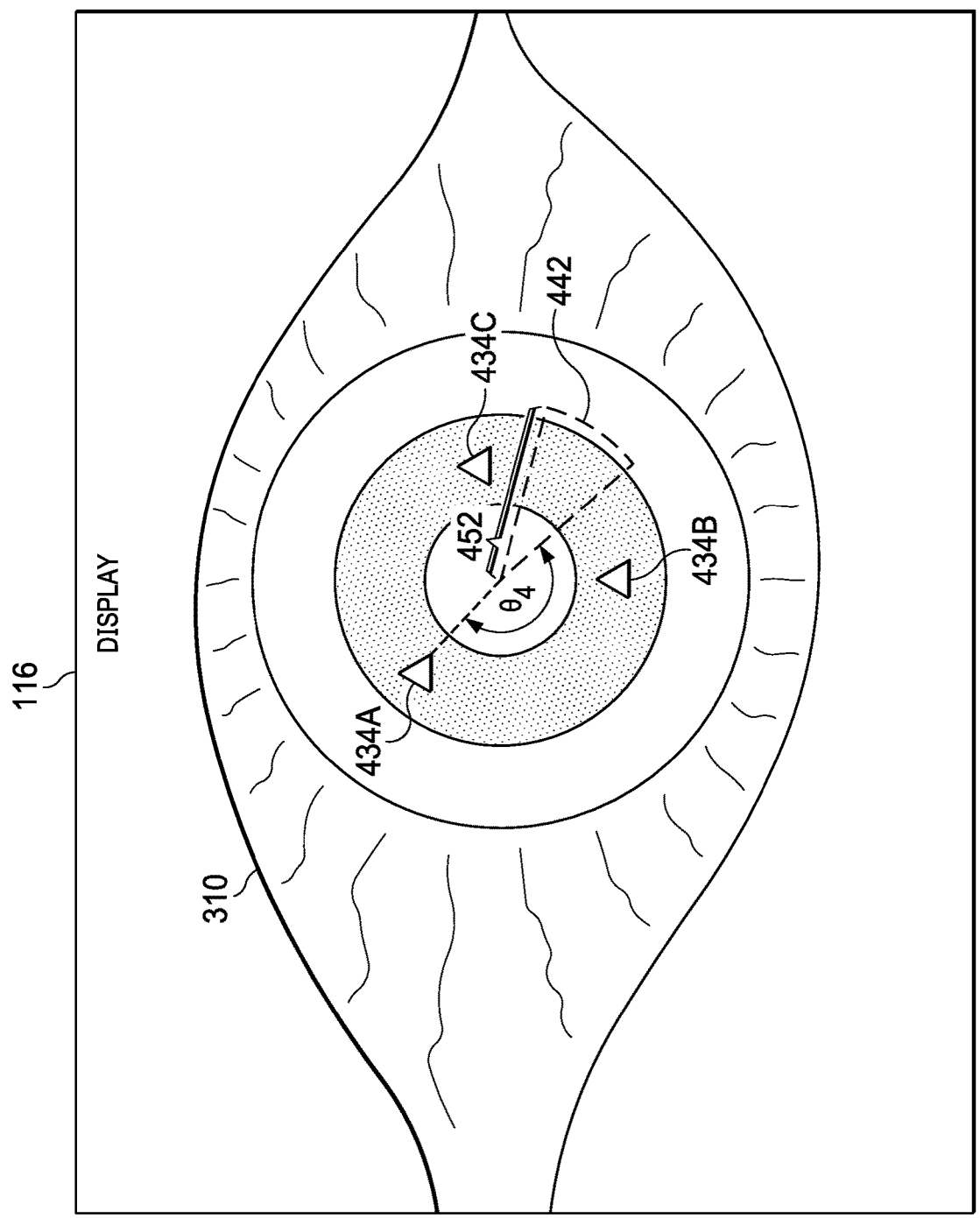
Figure 4E:
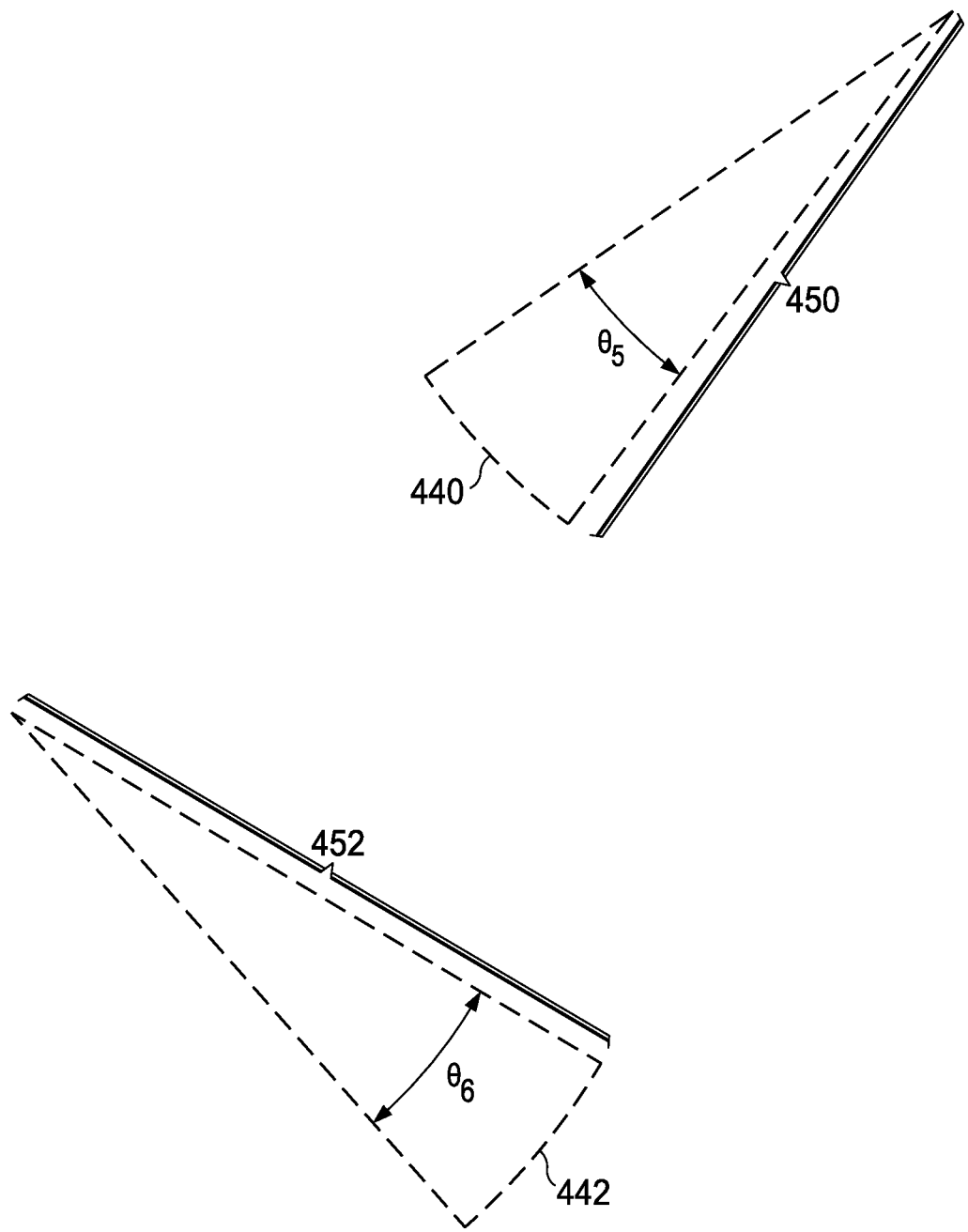

Turning now to FIGS. 4C-4E, examples of indicating incision sites are illustrated. As shown in FIG. 4C, display 116 may display an overlay 440 that may indicate a site of a first incision. In one example, overlay 440 may be located at an angular measurement $\theta_3$ from iris structure 434A, with respect to the center of pupil 405 of eye 122. In another example, overlay 440 may be located at a distance measurement 450 from the center of pupil 405 of eye 122. As illustrated in FIG. 4D, display 116 may display an overlay 442 that may indicate a site of a second incision. In one example, overlay 442 may be located at an angular measurement $\theta_4$ from iris structure 434A, with respect to the center of pupil 405 of eye 122. In another example, overlay 442 may be located at a distance measurement 452 from the center of pupil 405 of eye 122.

System 110 may utilize one or more of iris structures 434A-434C in determining one or more positions of one or more overlays 440 and 442, among others. In one example, system 110 may utilize angular measurement $\theta_3$ from iris structure 434A in displaying overlay 440. In another example, system 110 may utilize angular measurement $\theta_4$ from iris structure 434A in displaying overlay 442.

Figure 4F:
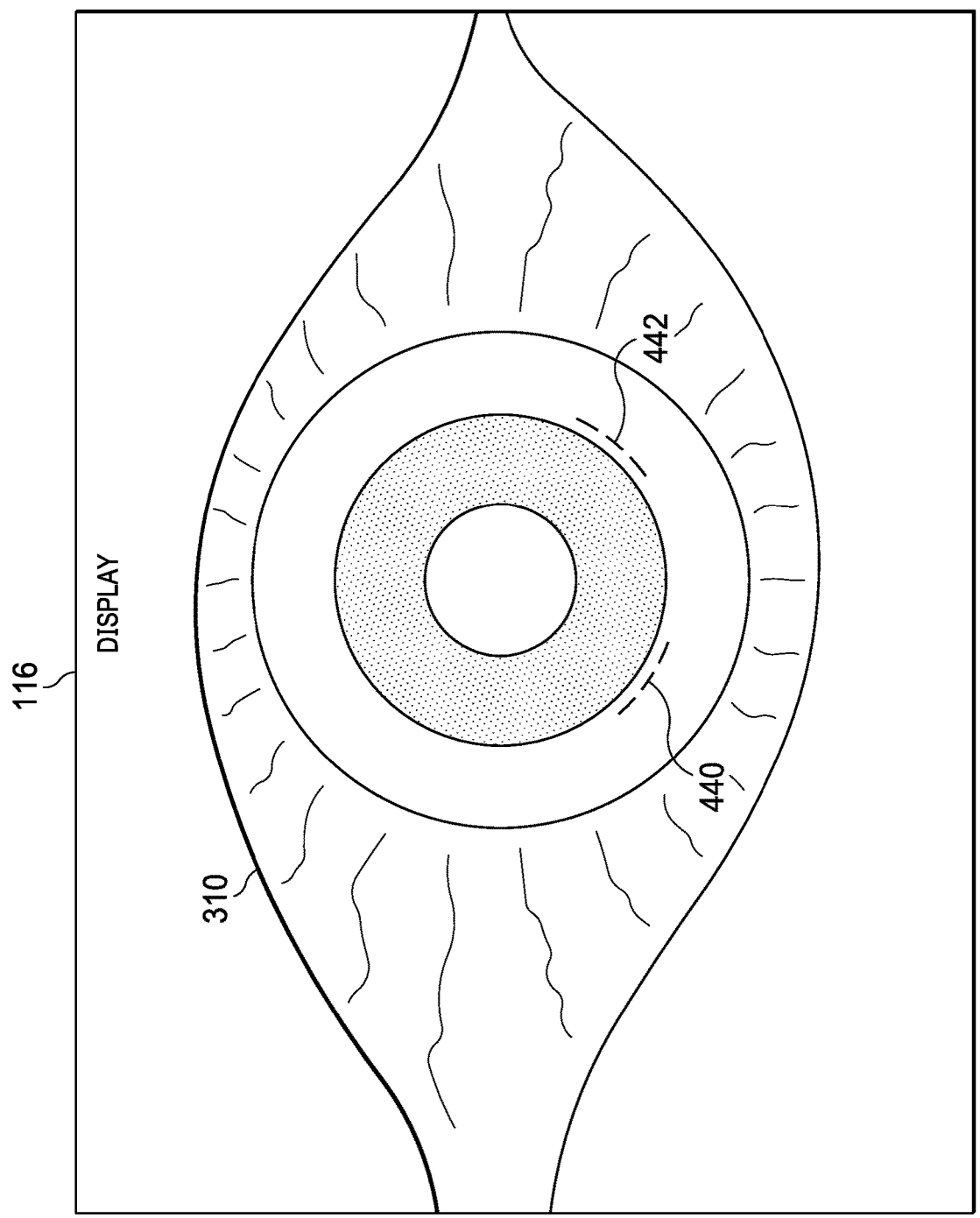
FIG. 4F illustrates an example of displaying multiple overlays that indicate respective multiple incision sites.

Overlay 440 may be associated with one or more of an angular measurement $\theta_5$ and a distance measurement 450, among others, as illustrated in FIG. 4E. For example, overlay 440 may be or include an arc. Overlay 442 may be associated with one or more of an angular measurement $\theta_6$ and a distance measurement 452, among others, as illustrated in FIG. 4E. For example, overlay 442 may be or include an arc. Display 416 may display overlays 440 and 442, as illustrated in FIG. 4F. For example, display 416 may concurrently display overlays 440 and 442. One or more of overlays 440 and 442 may aid a physician and/or a surgeon in finding one or more respective incision sites.

Figure 5:
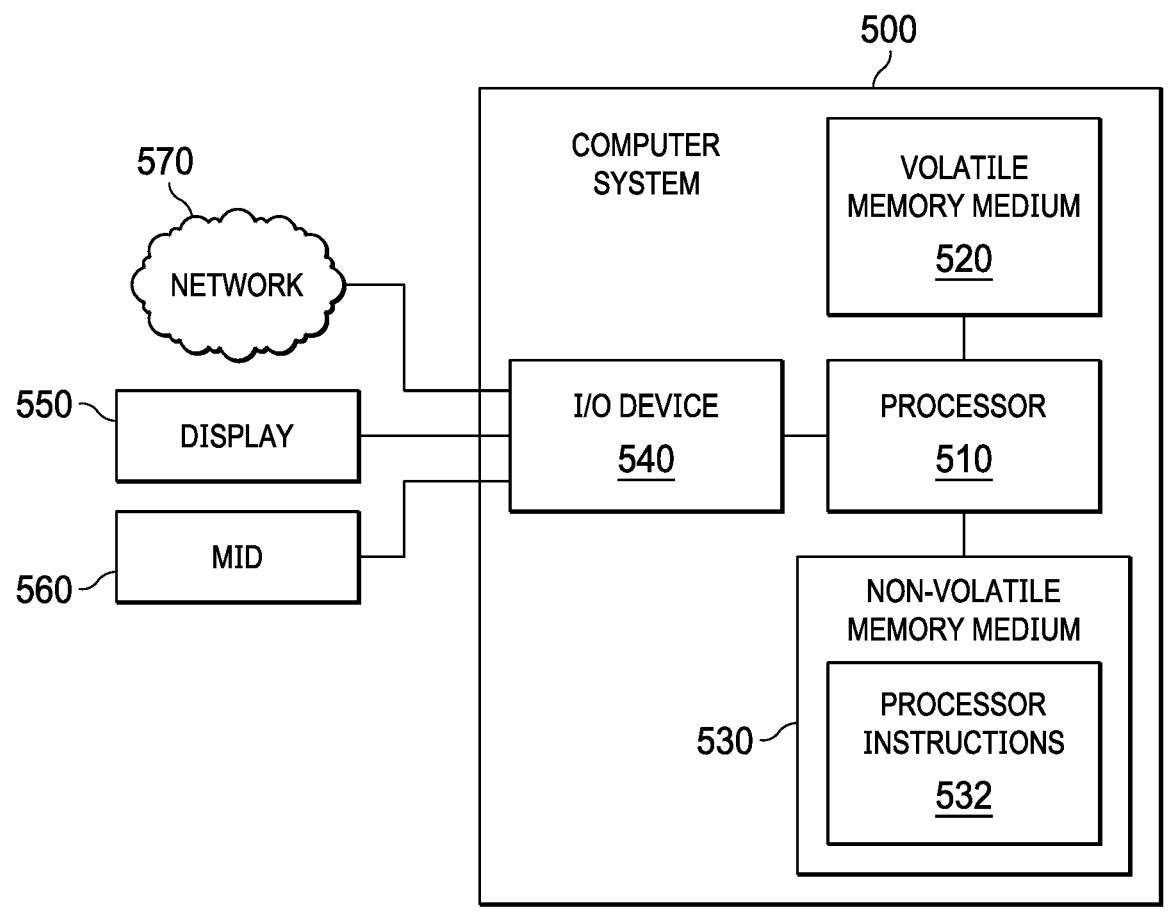
FIG. 5 illustrates an example of a computer system.

Turning now to FIG. 5, an example of a computer system is illustrated. As shown, a computer system 500 may include a processor 510, a volatile memory medium 520, a non-volatile memory medium 530, and an input/output (I/O) device 540. As illustrated, volatile memory medium 520, non-volatile memory medium 530, and I/O device 540 may be communicatively coupled to processor 510.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 530 may include processor instructions 532.

Processor instructions 532 may be executed by processor 510. In one example, one or more portions of processor instructions 532 may be executed via non-volatile memory medium 530. In another example, one or more portions of processor instructions 532 may be executed via volatile memory medium 520. One or more portions of processor instructions 532 may be transferred to volatile memory medium 520.

Processor 510 may execute processor instructions 532 in implementing at least a portion of one or more systems, one or more flow charts, one or more processes, and/or one or more methods described herein. For example, processor instructions 532 may be configured, coded, and/or encoded with instructions in accordance with at least a portion of one or more systems, one or more flowcharts, one or more methods, and/or one or more processes described herein. Although processor 510 is illustrated as a single processor, processor 510 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 510 may include any suitable system, device, or apparatus operable to interpret and execute program instructions, process data, or both stored in a memory medium and/or received via a network. Processor 510 further may include one or more microprocessors, microcontrollers, digital signal processors (DSPs), application specific integrated circuits (ASICs), or other circuitry configured to interpret and execute program instructions, process data, or both.

I/O device 540 may include any instrumentality or instrumentalities, which allow, permit, and/or enable a user to interact with computer system 500 and its associated components by facilitating input from a user and output to a user. Facilitating input from a user may allow the user to manipulate and/or control computer system 500, and facilitating output to a user may allow computer system 500 to indicate effects of the user's manipulation and/or control. For example, I/O device 540 may allow a user to input data, instructions, or both into computer system 500, and otherwise manipulate and/or control computer system 500 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 540 may include one or more busses, one or more serial devices, and/or one or more network interfaces, among others, that may facilitate and/or permit processor 510 to implement at least a portions of one or more systems, processes, and/or methods described herein. In one example, I/O device 540 may include a storage interface that may facilitate and/or permit processor 510 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 540 may include a network interface that may facilitate and/or permit processor 510 to communicate with a network. I/O device 540 may include one or more of a wireless network interface and a wired network interface. In a third example, I/O device 540 may include one or more of a peripheral component interconnect (PCI) interface, a PCI Express (PCIe) interface, a serial peripheral interconnect (SPI) interface, and an inter-integrated circuit (I²C) interface, among others. In a fourth example, I/O device 540 may include circuitry that may permit processor 510 to communicate data with one or more sensors. In a fifth example, I/O device 540 may facilitate and/or permit processor 510 to communicate data with one or more of a display 550 and a MID 560, among others. In another example, I/O device 540 may facilitate and/or permit processor 510 to communicate data with an imaging device 570. As illustrated, I/O device 540 may be coupled to a network 570. For example, I/O device 540 may include a network interface.

Network 570 may include a wired network, a wireless network, an optical network, or a combination of the foregoing, among others. Network 570 may include and/or be coupled to various types of communications networks. For example, network 570 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 500. In one example, computer system 112 may include one or more structures and/or one or more functionalities as those described with reference to computer system 500. In another example, a computer system of MID 250 may include one or more structures and/or one or more functionalities as those described with reference to computer system 500.

Figure 6A:
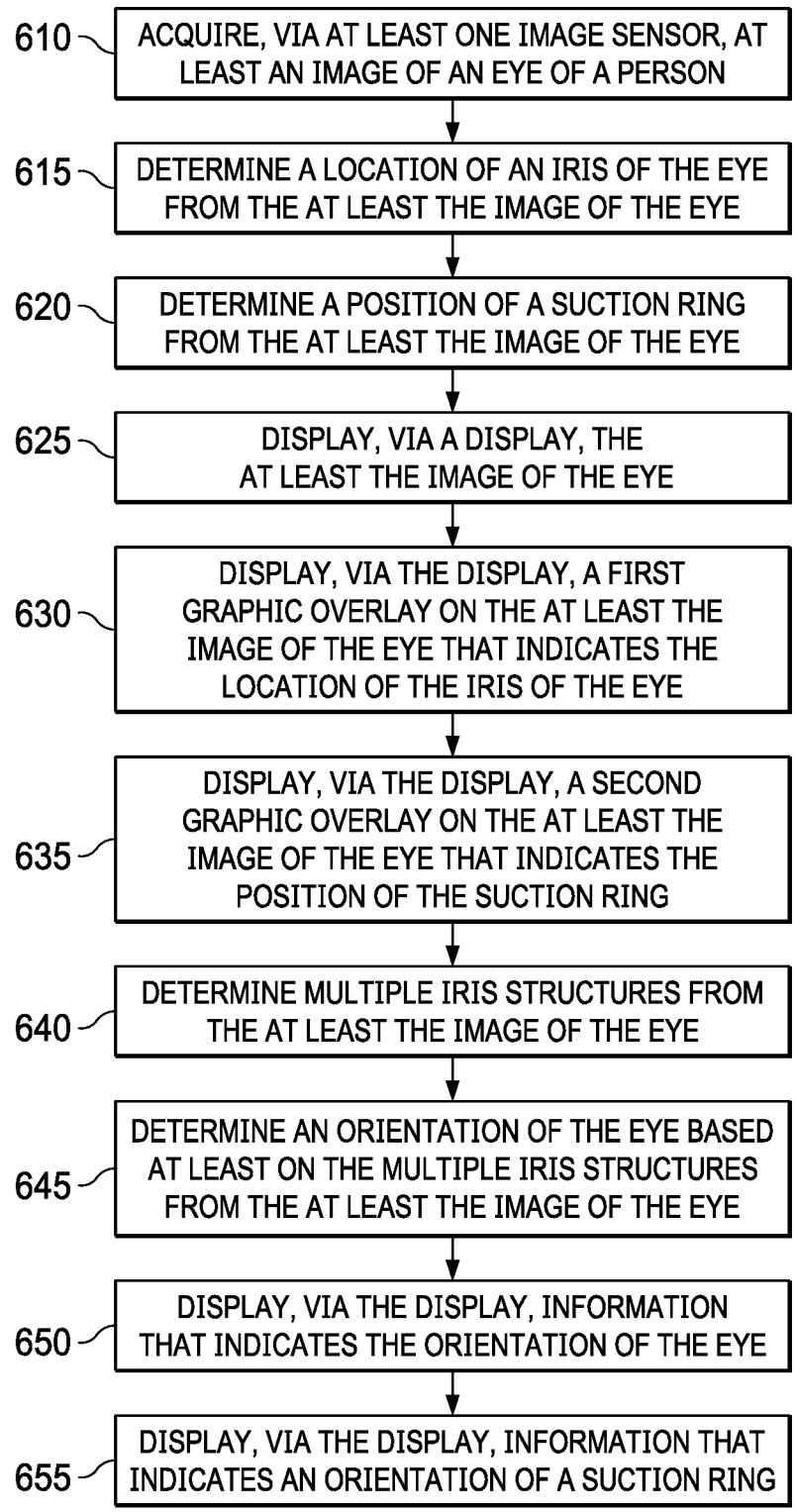
FIG. 6A illustrates an example of a method of operating a system.

Turning now to FIG. 6A, an example of a method of operating a system is illustrated. At 610, at least one image of an eye of a person may be acquired via at least one image sensor. In one example, the at least one image of the eye may include multiple images of the eye. In another example, the at least one image sensor may include multiple image sensors. An image sensor may be or include a camera.

At 615, a location of an iris of the eye may be determined from the at least the image of the eye. The location of the iris of the eye may include a boundary with a pupil of the eye. At 620, a position of a suction ring may be determined from the at least the image of the eye. At 625, the at least the image of the eye may be displayed via a display. For example, at least image 310 of eye 122 may be displayed via display 116. Although the examples and FIGS. utilize display 116, any image(s) and/or graphic(s) that display 116 may display, one or more of displays 262A and 262B of MID 250 may display in addition to display 116 or in place of display 116.

At 630, a first graphic overlay may be displayed on the at least the image of the eye that indicates the location of the iris of the eye. For example, graphic overlay 320, that indicates the location of the iris of the eye, may be displayed on image 310. The first graphic overlay may include a circular shape.

At 635, a second graphic overlay may be displayed on at least the image of the eye that indicates the position of the suction ring. In one example, graphic overlay 330A, that indicates the position of suction ring 140, may be displayed on image 310, as illustrated in FIG. 3C. In a second example, graphic overlay 330B, that indicates the position of suction ring 140, may be displayed on image 310, as illustrated in FIG. 3D. In a third example, graphic overlay 334A, that indicates the position of suction ring 140, may be displayed on image 310, as illustrated in FIG. 3E. In a fourth example, graphic overlay 334B, that indicates the position of suction ring 140, may be displayed on image 310, as illustrated in FIG. 3F. In another example, graphic overlay 334B, that indicates the position of suction ring 140, may be displayed on image 310, as illustrated in FIG. 3G. The second graphic overlay may include a circular shape.

At 640, multiple iris structures may be determined from the at least the image of the eye. For example, multiple of iris structures 434A-434C may be determined from image 310. At 645, an orientation of the eye may be determined based at least on the multiple iris structures from the at least the image of the eye. For example, an orientation of eye 122 may be determined based at least on the multiple of iris structures 434A-434C. An orientation of eye 122 may include a tilt. For example, the tilt may be in an x-direction and/or a y-direction. An orientation of eye 122 may include a rotation of eye 122. For example, eye 122 may exhibit cyclorotation.

At 650, information that indicates the orientation of the eye may be displayed. In one example, the information that indicates the orientation of eye 122 may include graphic overlay 324A, as illustrated in FIGS. 3E and 3F. In another example, the information that indicates the orientation of eye 122 may include graphic overlay 324B, as illustrated in FIG. 3G.

The information that indicates the orientation of the eye may include a third graphic overlay that represents a first reticle associated with an orientation of the eye. In one example, the information that indicates the orientation of eye 122 may include graphic overlay 324A that represents a first reticle associated with an orientation of eye 122, as illustrated in FIGS. 3E and 3F. In another example, the information that indicates the orientation of eye 122 may include graphic overlay 324B that represents a first reticle associated with an orientation of eye 122, as illustrated in FIG. 3G.

At 655, information that indicates an orientation of a suction ring may be displayed. The information that indicates the orientation of the suction ring may include a fourth graphic overlay. In one example, the information that indicates the orientation of suction ring 140 may include graphic overlay 334A, illustrated in FIGS. 3E and 3G. In another example, the information that indicates the orientation of suction ring 140 may include graphic overlay 334B.

The example of the method described with reference to FIG. 6A may be repeated. For example, eye 122 may not be or remain motionless. Eye 122 may move during a docking process. Eye 122 may move left and/or right during the docking process, may move up and/or down during the docking process, and/or may rotate clockwise and/or counterclockwise during the docking process. A system that utilizes the example of the method described with reference to FIG. 6A may determine one or more movements of eye 122 during the docking process. A system that utilizes the example of the method described with reference to FIG. 6A may determine one or more movements of suction ring 140 during the docking process. For example, the system may track eye 122 and/or suction ring 140.

Figure 6B:
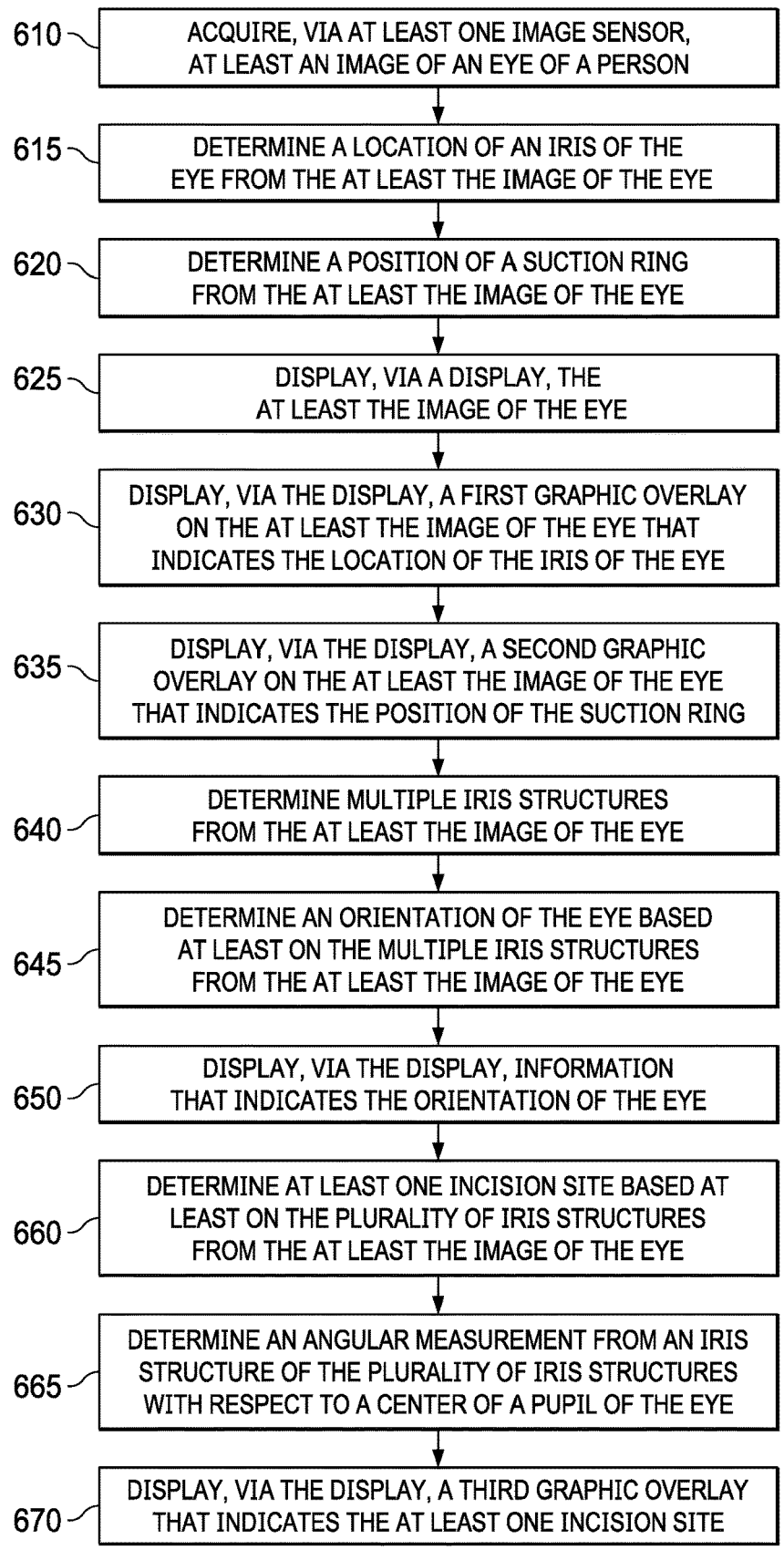
FIG. 6B illustrates another example of a method of operating a system.

Turning now to FIG. 6B, another example of a method of operating a system is illustrated. Method elements 610-650 of FIG. 6B may be performed in accordance with method elements 610-650 of FIG. 6A. At 660, at least one incision site may be determined based at least on the multiple iris structures from the at least the image of the eye. For example, at least one incision site may be determined based at least on the multiple of iris structures 434A-434C. One or more positions of one or more incision sites may be stored via a memory device. For example, the one or more positions of one or more incision sites may be based at least on multiple of iris structures 434A-434C.

At 665, an angular measurement may be determined from an iris structure of the multiple iris structures with respect to a center of a pupil of the eye. In one example, $\theta_3$ may be determined from iris structure 434A, as illustrated in FIG. 4C. In another example, $\theta_4$ may be determined from iris structure 434A, as illustrated in FIG. 4D.

At 670, a third graphic overlay that indicates the at least one incision site may be displayed via the display. In one example, graphic overlay 440, that indicates the at least one incision site, may be displayed via display 116, as illustrated in FIG. 4C. In another example, graphic overlay 442, that indicates the at least one incision site, may be displayed via display 116, as illustrated in FIG. 4D. Graphic overlays 440 and 442 may be displayed via display 116, as illustrated in FIG. 4F. For example, graphic overlays 440 and 442 may be concurrently displayed via display 116, as illustrated in FIG. 4F. Displaying the third graphic overlay that indicates the at least one incision site may be based at least on the angular measurement. In one example, displaying graphic overlays 440 may be based at least on $\theta_3$, as illustrated in FIG. 4C. In another example, displaying graphic overlays 442 may be based at least on $\theta_4$, as illustrated in FIG. 4D.

Displaying the third graphic overlay that indicates the at least one incision site may include displaying at least an arc of a circle that respectively indicates the at least one incision site. In one example, graphic overlay 440 may include at least an arc of a circle that respectively indicates the at least one incision site. In a second example, graphic overlay 442 may include at least an arc of a circle that respectively indicates the at least one incision site. In another example, graphic overlays 440 and 442 may include arcs of a circle that respectively indicates incision sites.

The example of the method described with reference to FIG. 6B may be repeated. For example, eye 122 may not be or remain motionless. Eye 122 may move. Eye 122 may move left and/or right, may move up and/or down, and/or may rotate clockwise and/or counterclockwise. A system that utilizes the example of the method described with reference to FIG. 6B may determine one or more movements of eye 122. For example, the system may track eye 122 and/or suction ring 140.

One or more of the method and/or process elements and/or one or more portions of a method and/or processor element may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:
   at least one processor;
   a display, coupled to the at least on processor;
   at least one image sensor, coupled to the at least on processor; and
   a memory medium that is coupled to the at least one processor and that includes instructions, when executed by the at least one processor, cause the medical system to:
   acquire, via the at least one image sensor, at least an image of an eye of a person;
   determine a location of an iris of the eye from the image of the eye;
   determine an x position, a y position, and a rotational orientation of a suction ring from the image of the eye, the x position, the y position, and the rotational orientation, each with respect to an optical axis of the suction ring;
   display, via the display, the image of the eye;
   display, via the display, a first graphic overlay on the image of the eye that indicates the location of the iris of the eye;
   display, via the display, a second graphic overlay comprising a reticle on the image of the eye that indicates the x position, the y position, and the rotational orientation of the suction ring when the suction ring is moved in a z-direction to the eye;
   determine a plurality of iris structures from the image of the eye;
   determine an orientation of the eye based at least on the plurality of iris structures from the image of the eye, the orientation of the eye comprising an x-direction tilt, a y-direction tilt, and a rotation of the eye, each with respect to an optical axis of the eye; and
   display, via the display, information that indicates the orientation of the eye to assist in docking the suction ring to the eye.

2. The medical system of claim 1, wherein the information that indicates the orientation of the eye includes a third graphic overlay that represents a second reticle associated with the orientation of the eye.

3. The medical system of claim 1, wherein the instructions further cause the medical system to:
   determine a location of a pupil of the eye from the image of the eye; and
   display, via the display, a third graphic overlay on the image of the eye that indicates the position of the location of the pupil of the eye.

4. The medical system of claim 1,
   wherein, to acquire the image of the eye of the person, the instructions further cause the medical system to acquire a plurality of images of the eye; and
   wherein the image of the eye of the person includes the plurality of images of the eye.

5. The medical system of claim 1, wherein the instructions further cause the medical system to:
   determine at least one incision site based at least on the plurality of iris structures from the image of the eye; and display, via the display, a third graphic overlay that indicates the at least one incision site.

6. The medical system of claim 5, wherein the instructions further cause the medical system to:
determine an angular measurement from an iris structure of the plurality of iris structures with respect to a center of a pupil of the eye;
wherein, to display, via the display, the third graphic overlay, the instructions further cause the system to display the third graphic overlay based at least on the angular measurement.

7. The medical system of claim 5, wherein, to display the third graphic overlay that indicates the at least one incision site, the instructions further cause the medical system to display at least an arc of a circle that respectively indicates the at least one incision site.

8. The medical system of claim 1, wherein at least one of the first graphic overlay and the second graphic overlay includes a circular shape.

9. A method, comprising:
acquiring, via at least one image sensor of the medical system, at least an image of an eye of a person;
determining a location of an iris of the eye from the image of the eye;
determining an x position, a y position, and a rotational orientation of a suction ring from the image of the eye, the x position, the y position, and the rotational orientation, each with respect to an optical axis of the suction ring;
displaying, via a display of the medical system, the image of the eye;
displaying, via the display, a first graphic overlay on the image of the eye that indicates the location of the iris of the eye;
displaying, via the display, a second graphic overlay comprising a reticle on the image of the eye that indicates the x position, the y position, and the rotational orientation of the suction ring when the suction ring is moved in a z-direction to the eye;
determining a plurality of iris structures from the image of the eye;
determining an orientation of the eye based at least on the plurality of iris structures from the image of the eye, the orientation of the eye comprising an x-direction tilt, a y-direction tilt, and a rotation of the eye, each with respect to an optical axis of the eye;
displaying, via the display, information that indicates the orientation of the eye, and
docking the suction ring to the eye based on the information that indicates the orientation of the eye.

10. The method of claim 9, wherein the information that indicates the orientation of the eye includes a third graphic overlay that represents a second reticle associated with the orientation of the eye.

11. The method of claim 9, further comprising:
determining a location of a pupil of the eye from the image of the eye; and
displaying, via the display, a third graphic overlay on the image of the eye that indicates the position of the location of the pupil of the eye.

12. The method of claim 9,
wherein acquiring the image of the eye of the person includes the medical system acquiring a plurality of images of the eye; and
wherein the image of the eye of the person includes the plurality of images of the eye.

13. The method of claim 9, further comprising:
determining at least one incision site based at least on the plurality of iris structures from the image of the eye; and
displaying, via the display, a third graphic overlay that indicates the at least one incision site.

14. The method of claim 13, further comprising:
determining an angular measurement from an iris structure of the plurality of iris structures with respect to a center of a pupil of the eye;
wherein displaying, via the display, the third graphic overlay is based at least on the angular measurement.

15. The method of claim 13, wherein displaying, via the display, the third graphic overlay that indicates the at least one incision site includes displaying at least an arc of a circle that respectively indicates the at least one incision site.

16. The method system of claim 9, wherein at least one of the first graphic overlay and the second graphic overlay includes a circular shape.

* * * * *